United States Patent
McGrane et al.

(10) Patent No.: US 12,161,136 B2
(45) Date of Patent: Dec. 10, 2024

(54) SCREENING METHODS USING GPRC6A TASTE RECEPTORS AND PET FOOD PRODUCTS AND COMPOSITIONS PREPARED USING THE SAME

(71) Applicant: MARS, INCORPORATED, McLean, VA (US)

(72) Inventors: Scott Joseph McGrane, Leicestershire (GB); Matthew Ronald Gibbs, Leicestershire (GB); Boris Klebansky, Oradell, NJ (US); Richard Masten Fine, Oradell, NJ (US)

(73) Assignee: MARS, INCORPORATED, McLean, VA (US)

( * ) Notice: Subject to any disclaimer, the term of this patent is extended or adjusted under 35 U.S.C. 154(b) by 946 days.

(21) Appl. No.: 17/252,069

(22) PCT Filed: Jun. 13, 2019

(86) PCT No.: PCT/US2019/037097
§ 371 (c)(1),
(2) Date: Dec. 14, 2020

(87) PCT Pub. No.: WO2019/241591
PCT Pub. Date: Dec. 19, 2019

(65) Prior Publication Data
US 2022/0087288 A1    Mar. 24, 2022

Related U.S. Application Data

(60) Provisional application No. 62/685,813, filed on Jun. 15, 2018.

(51) Int. Cl.
*A23K 50/40* (2016.01)
*A23K 20/142* (2016.01)
*A23K 40/00* (2016.01)
*G01N 33/566* (2006.01)

(52) U.S. Cl.
CPC ............ *A23K 50/40* (2016.05); *A23K 20/142* (2016.05); *A23K 40/00* (2016.05); *G01N 33/566* (2013.01)

(58) Field of Classification Search
CPC ...... A23K 50/40; A23K 20/142; A23K 40/00; G01N 33/566
See application file for complete search history.

(56) References Cited

U.S. PATENT DOCUMENTS 9,587,005 B2 * 3/2017 DiMarchi ................. A61P 1/14
2009/0014323 A1   1/2009 Yendler

FOREIGN PATENT DOCUMENTS

| EP | 1310174 A1 | 5/2003 | | |
|---|---|---|---|---|
| EP | 2 413 139 A1 | 2/2012 | | |
| EP | 2413139 B1 | 5/2015 | | |
| WO | 2008154286 A2 | 12/2008 | | |
| WO | WO-2010088633 A2 * | 8/2010 | .......... | G01N 33/502 |
| WO | 2014068045 A1 | 5/2014 | | |
| WO | 2014199114 A1 | 12/2014 | | |
| WO | WO-2016057996 A1 * | 4/2016 | .......... | G01N 33/566 |
| WO | WO 2018/094106 A2 | 5/2018 | | |
| WO | 2018094106 A3 | 8/2019 | | |

OTHER PUBLICATIONS

Altschul, et al., Basic Local Alignment Search Tool, J. Mol. Biol., vol. 215, Oct. 1990, pp. 403-410.
Altschul, et al., Gapped BLAST and PSI-BLAST: A New Generation of Protein Database Search Programs, Nucleic Acids Research, vol. 25, No. 17, Sep. 1997, pp. 3389-3402.
Anonymous, G-protein coupled receptor family C group 6 member A [Canis lupus fami—Protein-NCBI, UR:https://www.ncbi.nlm.nig.gov/protein/57032314, Retrieved from the Internet: Sep. 5, 2017,2 pgs.
Anonymous, G-Protein coupled receptor family C group 6 member A [Felis catus]—Protein-NCBI, URL:https://www.ncbi.nlm.nih.gov, Retrieved from the Internet: Dec. 12, 2017,2 pgs.
Anonymous, RecName: Full=G protein coupled receptor family C group 6 member A; Short=hGPRC6A; Alt Name; Full=G-protein coupled receptor GPCR33; Short=hGPCR33; Flags: Precursor—Protein—NCBI, Dec. 21, 2004, Retrieved from the Internet: URL: https://www.ncbi.nlm.nih.gov/protein/Q5T6X5, 6 pgs.
Cartoni, C., et al., Taste Preference for Fatty Acids is Mediated by GPR40 and GPR120, Journal of Neuroscience, Jun. 23, 2010, pp. 8376-8382, vol. 30, No. 25.
Cline, Perspectives for Gene Therapy: Inserting New Genetic Information into Mammalian Cells by Physical Techniques and Viral Vectors, Pharmac. Ther., 1985, pp. 69-92, vol. 29.
Cotten, et al., Receptor-Mediated Transport of DNA into Eurkaryotic Cells, Methods in Enzymology, Mar. 1993, pp. 618-644, vol. 217.
Cunningham, et al., High-Resolution Epitope Mapping of hGH-Receptor Interactions by Alanine-Scanning Mutagenesis, Science, Jun. 1989, pp. 1081-1085, Abstract only (2 pgs.), 244(4908).
Dore, et al., Structure of class C GPCR metabotropic glutamate receptor 5 transmembrane domain, Nature, Jul. 2014, 511(7511):557-62, (Abstract Only—2 pgs.).
Eswar, et al., Comparative Protein Structure Modeling Using Modeller, Current Protocols in Bioinformatics, Chapter 5: Unit—5.6, Supplement 15, 47 pages (Oct. 2006).

(Continued)

*Primary Examiner* — Brad Duffy
*Assistant Examiner* — Elizabeth A Shupe
(74) *Attorney, Agent, or Firm* — Baker Botts L.L.P.

(57) ABSTRACT

The presently disclosed subject matter relates to methods of screening raw materials and pet food products to manufacture a palatable pet food product. The presently disclosed subject matter also relates to methods for identifying compounds that modulate the activity and/or expression of a taste receptor.

9 Claims, 16 Drawing Sheets
Specification includes a Sequence Listing.

(56) References Cited

OTHER PUBLICATIONS

Geng, et al., Structural mechanism of ligand activation in human calcium-sensing receptor, eLife 5:e13662 (Jul. 19, 2016), 25 pages.
International Search Report and Written Opinion for PCT/US2019/037097, Nov. 11, 2019, 17 pgs.
Karlin, et al., Applications and Statistics for Multiple High-Scoring Segments in Molecular Sequences, Proc. Natl. Acad. Sci. USA vol. 90, Jun. 1993, pp. 5873-5877.
Karlin, et al., Methods for Assessing the Statistical Significance of Molecular Sequence Features by Using General Scoring Schemes, Proc. Natl. Acad. Sci. USA, Mar. 1990, pp. 2264-2268, vol. 87.
Lee, et al, Structural Insights into Ligand Recognition and Selectivity for Class A, B and C GPCR's, Dur. J. Pharmacol., Sep. 2015, 196-205, 763.
Loeffler, et al., Gene Transfer into Primary and Established Mammalian Cell Lines with Lipopolyamine-Coated DNA, Methods in Enzymology., Mar. 1993, pp. 599-618, vol. 217.
Myers, et al., Optical Alignments in Linear Space, Comput. Appl. Biosci., Mar. 1988, Abstract Only (1 pg.), 4 (1):11-17.
Pearson, et al., Improved Tools for Biological Sequence Comparison, Proc. Natl. Acad. Sci. USA, Apr. 1988, pp. 2444-2448, vol. 85.
Torelli, et al., ADVANCE an ADAM: two algorithms for the analysis of global similarity between homologous Informational sequences, Bioinformatics, Feb. 1994, pp. 3-5, vol. 10, No. 1.
Wu, et al., Structure of a Class C GPCR Metabotropic Glutamate Receptor 1 Bound to an Allosteric Modulator, Science, Apr. 2014, 58-64, 344(6179).
Pi, et al., Identification of a Novel Extracellular Cation-sensing G-protein coupled Receptor, J. Bio. Chem. Dec. 2, 2005; 280(48) 40201-40209.
Altschul et al., "Basic Local Alignment Search Tool," J. Mol. Biol. 215:403-410 (1990).
Altschul et al., "Gapped BLAST and PSI-BLAST: a new generation of protein database search programs," Nucleic Acids Res. 25:3389-3402 (1997).
Anonymous: "G-protein coupled receptor family C group 6 member A [Felis catus] Protein—NCBI", Dec. 12, 2017.
Anonymous: "G-protein coupled receptor family C group 6 member A [Canis lupus fami Protein—NCBI", Sep. 5, 2017 (Sep. 5, 2017).
Anonymous: "RecName: Full=G-protein coupled receptor family C group 6 member A; Sh—Protein—NCBI", Dec. 21, 2004.
Cartoni et al., "Taste Preference for Fatty Acids Is Mediated by GPR40 and GPR120," J. of Neuroscience, 30(25):8376-8382 (2010).
Cline, "Perspectives for Gene Therapy: Inserting New Genetic Information Into Mammalian Cells by Physical Techniques and Viral Vectors," Pharmac. Ther. 29:69-92 (1985).
Cotten et al., "Receptor-Mediated Transport of DNA into Eukaryotic Cells," Meth. Enzymol. 217:618-644 (1993).
Cunningham et al., "High-Resolution Epitope Mapping of hGH-Receptor Interactions by Alanine-Scanning Mutagenesis," Science 244:1081-1085 (1989).
Dore et al., "Structure of class C GPCR metabotropic glutamate receptor 5 transmembrane domain," Nature 511:557-562 (2014).
Eswar et al., "Comparative Protein Structure Modeling Using Modeller," Current Protocols in Bioinformatics, Supplement 15:5.6.1-5.6.30 (2006).
Geng et al., "Structural mechanism of ligand activation in human calcium-sensing receptor," eLIFE 5:e13662 (2016).
International Search Report mailed Nov. 11, 2019 in International Application No. PCT/US2019/037097.
Karlin et al., "Applications and statistics for multiple high-scoring segments in molecular sequences," Proc. Natl. Acad. Sci. USA 90:5873-5877 (1993).
Karlin et al., "Methods for assessing the statistical significance of molecular sequence features by using general scoring schemes," Proc. Natl. Acad. Sci. USA 87:2264-2268 (1990).
Lee et al., "Structural insights into ligand recognition and selectivity for class A, B, and C GPCRs," Eur J Pharmacol. 763:196-205 (2015).
Loeffler et al., "Gene Transfer into Primary and Established Mammalian Cell Lines with Lipopolyamine-Coated DNA," Meth. Enzymol. 217:599-618 (1993).
Myers et al., "Optimal alignments in linear space," CABIOS 4:11-17 (1988).
Pearson et al., "Improved tools for biological sequence comparison," Proc. Natl. Acad. Sci. USA 85:2444-2448 (1988).
Pi et al., "Identification of a Novel Extracellular Cation-sensing G-protein-coupled Receptor," The Journal of Biological Chemistry 280:40201-40209 (2005).
Torelli et al., "ADVANCE and ADAM: two algorithms for the analysis of global similarity between homologous informational sequences," Comput. Appl. Biosci., 10:3-5 (1994).
Wu et al., "Structure of a Class C GPCR Metabotropic Glutamate Receptor 1 Bound to an Allosteric Modulator," Science 344:58-64 (2014).

* cited by examiner

Figure 1

Cat, Dog and Human GPRC6A Receptor Nucleotide Sequences and Corresponding Amino Acid Sequences

Cat GPRC6A nucleotide sequence (SEQ ID NO:1)

atggcactattgattacactgattacctgttttgtgattcctcttgctacttcccagacttgccagaccccctgacgacttcgtggctgccacttctccaggg
catgtcataattggaggtttattcgccattcatgaaaaaatgctgtcctcagaagactatcccagacgaccagaaatccagaagtgtgttgggtttgaa
atatcaattttcttcaaactcttgccatgattcacagcattgagatgatcaataattcaacactattatctggaatcaaactggggtatgaaatctatgaca
cttgtacagaagtcacagtggcaatggcagccgctctgaggtttcttctaagttcaacagctccagagaaatcatggagtttaaatgtgactattccag
ctacatgccaagggttaaggctgtcataggtgctggctactcagaaataaccatggctgtctccaggatgttgaatttacagcttatgccacaggtga
gttatgaatcaactgcagaaatcctaagtgacaaaattcgctttccttcattttacggactgtgcccagtgacttctatcaaactaaagcaatggcccac
ctgattgagaagtctggatggaactggattggcatcatagccacagatgatgactatggacgaatggccctcaacacttttgcagttcagaccacag
caaataatgtgtgcatagctttcaaagaagttctcccagccttcctctcagataataccatcgaagtcaggatcaatgagacacttgagaaaatcatag
cagaagcccaggttaatgtcattgtggtattcctgaggcaattccatgttttcaatctcttcagtaaagctctagaaaggaatataaataagatatggatt
gctagtgataactggtcaacggccaccaagattacaaccattcctaatgttaaaaggattggcaaagttgtagggtttaccttagaagagggaatatg
tcttccttccattcctttcttcaaaatctgcatatatttcccagtgataataacaaggtcttaaatgaatatgccacactcttgtctgcttgtgcatatgtcaag
gacagtgatttgagtcagtgcatttccaaccattctcaggggactttggcctacaaggttaacaaggatatagaaaggaacttctccctgagaaatgat
ttcctgtggaattatactgagccaggccttgttcacagtatccagcttgcagtacttgctcttggttatgccattcgggatctctgccaagctcgcgactg
tcagaaccccaacgcctttcaaccatgggagttacttgatgcactaaaaaatgtgacattcactgatgaagggaattcatttcattttgatgctcatggg
gatatgaatactggatatgatgttgtgctctggaaggagattgatggtcacctgactatcaccaagatagcacaatatgatctgaagaatgatgtcttcg
tcatcacagaccaagaaacaaaaaatgagttcagaaatcttaagcaaattcagtctaaatgctccaaggagtgcagtcctgggcaaatgaagaaaa
ctacaagaagtcaacatatctgctgctatgaatgtgtgaactgtcctgaaaatcactacagtaaccagacagatatggatcactgcctttatgtaacaa
cgaaactcagtgggcccctgtaaagagcacagcatgctttgaaaaggaagtggagtatctcagttggaatgactccttggccatactgctcctggcc
ctctccctactaggaatcatgtttgttctggccattggcataatatttacaagaaacctgaacacgcctgttgtgaaatcgtccgggggattgctggtctg
ctatgtgatccttctctgtcatttcctcaactttgccagcacgggcttttcattggagaaccacaagacttcacatgtaaaaccaggcagacgttttttgg
tgtgagcttcactctctgcatctcctgcattttggtgaagtccctgaaaattctgctagccttcagcttcgaccccaagttgcagaacttcctgaagtgcc
tctataaacccatccccatcatcttcatttgcacaggtatccaggttgccatttgcacagtctggctaatctttgcagcacctgctgtggaagagaatgtc
tccttgcccagagtcattatcctggaatgtgaggagggatccatccttgcatttggcatcatgctgggctatattgccatcctggccttcatttgcttcata
tttgccttcaaaggcaggaaactacccgagaattacaatgaagccaaattcataacatttggcatgctcgtttatttcatagcttggatcacattcgtccc
cgtctatgctaccacatttggtaaatatttaccagctgtggagattatcattattttaatatcgaactatgggatcctgtgttgcacattcttccccaaatgct
atgttattctttataagcaggagactaacacaaaatctgcctttctcaagatgatttacagttactcttcccacagcgcaagcagccttgccatgagtcac
gtttccctggactcctctagcagcaacatcacagcgaccaatcccagctccggtggcaggcctgcagcctggcaggaaagcagggatatccggg
cacaagcatttgcacacacacgcagagaaaacgctgcaagtatgtctaaaacttggcctcggaaaagaatttcaagtatttga

Dog GPRC6A nucleotide sequence (SEQ ID NO:2)

atggcactattgattataccgattacctgctttgggagtactcttgttacttcccagccttgccagactcctgatgactttgtggctgccacttctccagga
catatcatgattggaggtttatttgccattcatgagaaaatgctgccctcagaagactatcccagacgaccagaaatccagaagtgtgttggctttgaa
atatcaattttcttcaaactcttgccatgattcatagcattgagatgatcaacaattcaacactattatccggagtcaaactggggtatgaaatctatgac
acctgtaccgaagtcacagtggcgatggcagccactctgaggtttctctctaagcgcaactgctccagagaaattgtggagtttaagtgtgattattcc
agctacatgccaagagttaaggctgtataggtgctggctactcagaaataacaatggctgtctccaggatgctgaatttacagctcatgccacaggt
gagttatgaatcaactgcagaaatcctaagtgacaaaattcgctttccttcattttacggactgtgcccagtgacttctatcaaactaaagcaatggccc
acctgattcagaaatctggatggaactggattggcatcatagccacagatgatgactacggacgactggccctcaacacttttgcagttcagaccgc
agcaaataatgtgtgcatagctttcaaggaggttctcccagccttcctctcagatgataccattgaaatcaggatcaatgagacccttgagaaaatcat
cgcagaagcccaggttaatgtcattgtggtatttctgaggcaattccatgttttcaatctcttcactaaagctatagaaaagaatataaataagatctggat
tgccagtgataactggtccatggccaccaagatcaccaccatccctaatgttaaaaggattggcaaagttgtggggtttaccttagaagagggaata
tgtcttctttccactccttcttcaaaacttgcatatgtttcccagagataataacaaggcccctaaatgaatatgccatgctcttgtctgcctgtgcacatgtc
aaggacagtgatttgagtcagtgcatttccagccgctctcgggggactttggcctacacggctaacaaggatatagaaaggaacttctccctgagaa
atgatttcctgtgggattacaccgagccgggacctgttcacagtatccagctcgcagttcttgcccttggttatgccattcgggatctctgccaagctcg
agactgtcagaaccccaacgcctttcaaccatgggagttacttgatgtattaaaaaatgtgacattcactgatgaagggaattcatttcattttgatgccc
atggggatatgaatactggatatgatgttgtgctctggaaggagattggc

Figure 1 Continued ggccacatgactatcaccaagatggcacaatatgatctgaggaatgatgtcttcatcatcacagaccaagaaacaaaaaatgagttcagaaatcttaa
gcaaattcgatctaaatgctccaaggaatgcagtcctgggcaaatgaaaaaaactacaagaagtcaacatatctgctgctatgaatgtgtggactgtc
ctgaaaatcactacagtaaccagacagatatggatcactgcctcttatgcaacaatgaaactcactgggcccctgtcaggagcacaaggtgctttga
aaaggaagtggaatatctcaactggaatgattccttggctatactgctcctggccctctccctactaggaatcatccttgttctggccattggcataatat
ttacaagaaacctgaacacacccattgtaaaatcatctgggggattgctggtctgctacgtgatccttctctgtcatgtcctcaacttcgccagcacagg
cttcttcattggagaaccacaagacttcacatgtaaaaccaggcagactgtatttggtgtgagcttcactctctgcatctcctgcattttgatgaagtccct
gaaaattctgctagccttcagcttcgatcccaagttgcagaacttcttgaagtgcctctataaaccgatccccatcatcttcacttgcacaggtatccag
gttgtcatttgcacaatctggctaatctttgcagcacctgctgtggaagagaatgtctccttgcccagagtcattatcctggaatgtgaggagggatcc
gtccttgcatttggcaccatgctgggttatattgccatcctggccttcatttgcttcatatttgcattcaaaggcaggaaattacctgagcattacaacgaa
gccaaattcataacatttggcatgctcatttatttcatagcttggatcacattcatccccatctatgctaccacatttggtaaatatttgccagctgtggaga
ttattgttattttaatttctaactatgggatcctgtgttgcacattcttccccaaatgctatattattctttgtaagcaagaggctaacacaaaatctgcctttct
caagatgatttacagttactcttcccacactgcaagcagccttgccattagtcatgtttcactggactccactaacagcagtatcacaacgaccaatccc
agctctagtggcaagtctgcagcctggcaggaaagcaaggatcttcaggcacaagcatttgcacacatatgcagagaaaatgcgataagtgtacct
aaaattttacctcgaaaaagaatttcaagtatatga

Human GPRC6A nucleotide sequence (SEQ ID NO:3)

atggcattcttaattatactaattacctgctttgtgattattcttgctacttcacagccttgccagacccctgatgactttgtggctgccacttctccgggaca
tatcataattggaggtttgtttgctattcatgaaaaaatgttgtcctcagaagactctcccagacgaccacaaatccaggagtgtgttggctttgaaatat
cagtttttcttcaaactcttgccatgatacacagcattgagatgatcaacaattcaacactcttacctggagtcaaactggggtatgaaatctatgacactt
gtacagaagtcacagtggcaatggcagccactctgaggtttctttctaaattcaactgctccagagaaactgtggagtttaagtgtgactattccagcta
catgccaagagttaaggctgtcataggttctgggtactcagaaataactatggctgtctccaggatgttgaatttacagctcatgccacaggtgggttat
gaatcaactgcagaaatcctgagtgacaaaattcgctttccttcatttttacggactgtgcccagtgacttccatcaaattaaagcaatggctcacctgat
tcagaaatctggttggaactggattggcatcataaccacagatgatgactatggacgattggctcttaacactttataattcaggctgaagcaaataac
gtgtgcatagccttcaaagaggttcttccagcctttctttcagataataccattgaagtcagaatcaatcggacactgaagaaaatcattttagaagccc
aggttaatgtcattgtggtatttctgaggcaattccatgttttgatctcttcaataaagccattgaaatgaatataaataagatgtggattgctagtgataat
tggtcaactgccaccaagattaccaccattcctaatgttaaaaagattggcaaagttgtagggtttgcctttagaagagggaatatatcctctttccattc
ctttcttcaaaatctgcacttgcttcccagtgacagtcacaaactcttacatgaatatgccatgcatttatctgcctgcgcatatgtcaaggacactgattt
gagtcaatgcatattcaatcattctcaaaggactttggcctacaaggctaacaaggctatagaaaggaacttcgtcatgagaaatgacttcctctggga
ctatgctgagccaggactcattcatagtattcagcttgcagtgtttgcccttggttatgccattcgggatctgtgtcaagctcgtgactgtcagaacccca
acgcctttcaaccatgggagttacttggtgtgctaaaaaatgtgacattcactgatggatggaattcatttcatttgatgctcacggggatttaaatactg
gatatgatgttgtgctctggaaggagatcaatggacacatgactgtcactaagatggcagaatatgacctacagaatgatgtcttcatcatcccagatc
aggaaacaaaaaatgagttcaggaatcttaagcaaattcaatctaaatgctccaaggaatgcagtcctgggcaaatgaagaaaactacaagaagtc
aacacatctgttgctatgaatgtcagaactgtcctgaaaatcattacactaatcagacagatatgcctcactgccttttatgcaacaacaaaactcactg
ggcccctgttaggagcactatgtgctttgaaaaggaagtggaatatctcaactggaatgactccttggccatcctactcctgattctctccctactggga
atcatatttgttctggttgttggcataatatttacaagaaacctgaacacacctgttgtgaaatcatccggggggattaagagtctgctatgtgatccttctct
gtcatttcctcaattttgccagcacgagcttttcattggagaaccacaagacttcacatgtaaaaccaggcagacaatgtttggagtgagctttactcttt
gcatcctgcatttgacgaagtctctgaaaattttgctagccttcagctttgatcccaaattacagaaatttctgaagtgcctctatagaccgatccttat
tatcttcacttgcacgggcatccaggttgtcatttgcacactctggctaatctttgcagcacctactgtagaggtgaatgtctccttgcccagagtcatca
tcctggagtgtgaggagggatccatacttgcatttggcaccatgctgggctacattgccatcctggccttcatttgcttcatatttgctttcaaaggcaaa
tatgagaattacaatgaagccaaattcattacatttggcatgctcatttacttcatagcttggatcacattcatccctatctatgctaccacatttggcaaat
atgtaccagctgtggagattattgtcatattaatatctaactatggaatcctgtattgcacattcatcccaaatgctatgttattatttgtaagcaagagatt
aacacaaagtctgcctttctcaagatgatctacagttattcttcccatagtgtgagcagcattgccctgagtcctgcttcactggactccatgagcggca
atgtcacaatgaccaatcccagctctagtggcaagtctgcaacctggcagaaaagcaaagatcttcaggcacaagcatttgcacacatatgcaggg
aaaatgccacaagtgtatctaaaactttgcctcgaaaaagaatgtcaagtatatga

Figure 1 Continued

<u>Cat GPRC6A amino acid sequence (SEQ ID NO:4)</u>
MALLITLITCFVIPLATSQTCQTPDDFVAATSPGHVIIGGLFAIHEKMLSSEDYPRRPEIQKCVG
FEISIFLQTLAMIHSIEMINNSTLLSGIKLGYEIYDTCTEVTVAMAAALRFLSKFNSSREIMEFKC
DYSSYMPRVKAVIGAGYSEITMAVSRMLNLQLMPQVSYESTAEILSDKIRFPSFLRTVPSDFY
QTKAMAHLIEKSGWNWIGIIATDDDYGRMALNTFAVQTTANNVCIAFKEVLPAFLSDNTIEV
RINETLEKIIAEAQVNVIVVFLRQFHVFNLFSKALERNINKIWIASDNWSTATKITTIPNVKRIG
KVVGFTFRRGNMSSFHSFLQNLHIFPSDNNKVLNEYATLLSACAYVKDSDLSQCISNHSQGTL
AYKVNKDIERNFSLRNDFLWNYTEPGLVHSIQLAVLALGYAIRDLCQARDCQNPNAFQPWE
LLDALKNVTFTDEGNSFHFDAHGDMNTGYDVVLWKEIDGHLTITKIAQYDLKNDVFVITDQ
ETKNEFRNLKQIQSKCSKECSPGQMKKTTRSQHICCYECVNCPENHYSNQTDMDHCLLCNNE
TQWAPVKSTACFEKEVEYLSWNDSLAILLLALSLLGIMFVLAIGIIFTRNLNTPVVKSSGGLLV
CYVILLCHFLNFASTGFFIGEPQDFTCKTRQTFFGVSFTLCISCILVKSLKILLAFSFDPKLQNFL
KCLYKPIPIIFICTGIQVAICTVWLIFAAPAVEENVSLPRVIILECEEGSILAFGIMLGYIAILAFIC
FIFAFKGRKLPENYNEAKFITFGMLVYFIAWITFVPVYATTFGKYLPAVEIIIILISNYGILCCTFF
PKCYVILYKQETNTKSAFLKMIYSYSSHSASSLAMSHVSLDSSSSNITATNPSSGGRPAAWQE
SRDIRAQAFAHTRRENAASMSKTWPRKRISSI <u>Dog GPRC6A amino acid sequence (SEQ ID NO:5)</u>
MALLIIPITCFGSTLVTSQPCQTPDDFVAATSPGHIMIGGLFAIHEKMLPSEDYPRRPEIQKCVG
FEISIFLQTLAMIHSIEMINNSTLLSGVKLGYEIYDTCTEVTVAMAATLRFLSKRNCSREIVEFK
CDYSSYMPRVKAVIGAGYSEITMAVSRMLNLQLMPQVSYESTAEILSDKIRFPSFLRTVPSDF
YQTKAMAHLIQKSGWNWIGIIATDDDYGRLALNTFAVQTAANNVCIAFKEVLPAFLSDDTIEI
RINETLEKIIAEAQVNVIVVFLRQFHVFNLFTKAIEKNINKIWIASDNWSMATKITTIPNVKRIG
KVVGFTFRRGNMSSFHSFLQNLHMFPRDNNKPLNEYAMLLSACAHVKDSDLSQCISSRSRGT
LAYTANKDIERNFSLRNDFLWDYTEPGPVHSIQLAVLALGYAIRDLCQARDCQNPNAFQPWE
LLDVLKNVTFTDEGNSFHFDAHGDMNTGYDVVLWKEIGGHMTITKMAQYDLRNDVFIITDQ
ETKNEFRNLKQIRSKCSKECSPGQMKKTTRSQHICCYECVDCPENHYSNQTDMDHCLLCNNE
THWAPVRSTRCFEKEVEYLNWNDSLAILLLALSLLGIILVLAIGIIFTRNLNTPIVKSSGGLLVC
YVILLCHVLNFASTGFFIGEPQDFTCKTRQTVFGVSFTLCISCILMKSLKILLAFSFDPKLQNFL
KCLYKPIPIIFTCTGIQVVICTIWLIFAAPAVEENVSLPRVIILECEEGSVLAFGTMLGYIAILAFI
CFIFAFKGRKLPEHYNEAKFITFGMLIYFIAWITFIPIYATTFGKYLPAVEIIVILISNYGILCCTFF
PKCYIILCKQEANTKSAFLKMIYSYSSHTASSLAISHVSLDSTNSSITTTNPSSSGKSAAWQESK
DLQAQAFAHICRENAISVPKILPRKRISSI <u>Human GPRC6A amino acid sequence (SEQ ID NO:6)</u>
MAFLIILITCFVIILATSQPCQTPDDFVAATSPGHIIIGGLFAIHEKMLSSEDSPRRPQIQECVGFEI
SVFLQTLAMIHSIEMINNSTLLPGVKLGYEIYDTCTEVTVAMAATLRFLSKFNCSRETVEFKC
DYSSYMPRVKAVIGSGYSEITMAVSRMLNLQLMPQVGYESTAEILSDKIRFPSFLRTVPSDFH
QIKAMAHLIQKSGWNWIGIITTDDDYGRLALNTFIIQAEANNVCIAFKEVLPAFLSDNTIEVRI
NRTLKKIILEAQVNVIVVFLRQFHVFDLFNKAIEMNINKMWIASDNWSTATKITTIPNVKKIGK
VVGFAFRRGNISSFHSFLQNLHLLPSDSHKLLHEYAMHLSACAYVKDTDLSQCIFNHSQRTLA
YKANKAIERNFVMRNDFLWDYAEPGLIHSIQLAVFALGYAIRDLCQARDCQNPNAFQPWEL
LGVLKNVTFTDGWNSFHFDAHGDLNTGYDVVLWKEINGHMTVTKMAEYDLQNDVFIIPDQ
ETKNEFRNLKQIQSKCSKECSPGQMKKTTRSQHICCYECQNCPENHYTNQTDMPHCLLCNNK
THWAPVRSTMCFEKEVEYLNWNDSLAILLLILSLLGIIFVLVVGIIFTRNLNTPVVKSSGGLRV
CYVILLCHFLNFASTSFFIGEPQDFTCKTRQTMFGVSFTLCISCILTKSLKILLAFSFDPKLQKFL
KCLYRPILIIFTCTGIQVVICTLWLIFAAPTVEVNVSLPRVIILECEEGSILAFGTMLGYIAILAFIC
FIFAFKGKYENYNEAKFITFGMLIYFIAWITFIPIYATTFGKYVPAVEIIVILISNYGILYCTFIPKC
YVIICKQEINTKSAFLKMIYSYSSHSVSSIALSPASLDSMSGNVTMTNPSSSGKSATWQKSKDL
QAQAFAHICRENATSVSKTLPRKRMSSI

|  | 1 | | | | | | | | | 10 | | | | | | | | | 20 | |
|---|---|---|---|---|---|---|---|---|---|---|---|---|---|---|---|---|---|---|---|---|
| hGPRC6A | M | A | L | I | I | I | T | C | F | V | I | L | A | T | S | Q | P | C | Q | T |
| cGPRC6A | M | A | L | I | I | I | T | C | F | L | I | L | V | T | S | Q | P | C | Q | T |
| fGPRC6A | M | A | L | L | I | I | T | C | F | V | I | P | L | A | T | S | Q | T | C | Q | T |

|  | | | | | | | | | | 90 | | | | | | | | | 100 | |
|---|---|---|---|---|---|---|---|---|---|---|---|---|---|---|---|---|---|---|---|---|
| hGPRC6A | I | E | M | I | N | N | S | T | L | L | S | G | V | K | L | G | Y | E | I | Y | D | T | C |
| cGPRC6A | I | E | M | I | N | N | S | T | L | L | S | G | V | K | L | G | Y | E | I | Y | D | T | C |
| fGPRC6A | I | E | M | I | N | N | S | T | L | L | S | G | I | K | L | G | Y | E | I | Y | D | T | C |

|  | | | | | | | | | | 170 | | | | | | | | | 180 | |
|---|---|---|---|---|---|---|---|---|---|---|---|---|---|---|---|---|---|---|---|---|
| hGPRC6A | L | Q | L | M | P | Q | V | Y | E | S | T | A | E | I | L | S | D | K | I | R | F | P |
| cGPRC6A | L | Q | L | M | P | Q | V | Y | E | S | T | A | E | I | L | S | D | K | I | R | F | P |
| fGPRC6A | L | Q | L | M | P | Q | V | Y | E | S | T | A | E | I | L | S | D | K | I | R | F | P |

|  | | | | | | | | | | 250 | | | | | | | | | 260 | |
|---|---|---|---|---|---|---|---|---|---|---|---|---|---|---|---|---|---|---|---|---|
| hGPRC6A | F | K | E | V | L | P | A | F | L | S | D | N | T | I | E | V | R | I | N | T | L |
| cGPRC6A | F | K | E | V | L | P | A | F | L | S | D | T | I | E | V | R | I | N | T | L |
| fGPRC6A | F | K | E | V | L | P | A | F | L | S | D | N | T | I | E | V | R | I | N | T | L |

|  | | | | | | | | | | 330 | | | | | | | | | 340 | |
|---|---|---|---|---|---|---|---|---|---|---|---|---|---|---|---|---|---|---|---|---|
| hGPRC6A | G | K | V | V | G | F | A | F | R | R | G | N | S | S | F | H | S | F | L | Q | N | L |
| cGPRC6A | G | K | V | V | G | F | F | R | R | G | N | S | S | F | H | S | F | L | Q | N | L |
| fGPRC6A | G | K | V | V | G | F | F | R | R | G | N | S | S | F | H | S | F | L | Q | N | L |

|  | | | | | | | | | | 410 | | | | | | | | | 420 | |
|---|---|---|---|---|---|---|---|---|---|---|---|---|---|---|---|---|---|---|---|---|
| hGPRC6A | D | F | L | W | Y | E | P | G | L | H | S | I | Q | L | A | V | A | L | G |
| cGPRC6A | D | F | L | W | Y | E | P | G | V | H | S | I | Q | L | A | V | A | L | G |
| fGPRC6A | D | F | L | W | Y | E | P | G | H | S | I | Q | L | A | V | A | L | G |

(A)

|  | | | | | | | | | | 490 | | | | | | | | | 500 | |
|---|---|---|---|---|---|---|---|---|---|---|---|---|---|---|---|---|---|---|---|---|
| hGPRC6A | E | I | G | H | T | T | K | A | Y | D | L | N | D | V | F | I |
| cGPRC6A | E | I | G | H | T | T | K | A | Y | D | L | N | D | V | F | I |
| fGPRC6A | E | I | G | H | L | T | T | K | A | Y | D | L | N | D | V | F | I |

|  | | | | | | | | | | 570 | | | | | | | | | 580 | |
|---|---|---|---|---|---|---|---|---|---|---|---|---|---|---|---|---|---|---|---|---|
| hGPRC6A | H | C | L | L | C | N | N | T | W | A | P | V | S | T | C | F | E | K | E |
| cGPRC6A | H | C | L | L | C | N | N | T | W | A | P | V | S | T | C | F | E | K | E |
| fGPRC6A | H | C | L | L | C | N | N | T | W | A | P | V | K | S | T | A | C | F | E | K | E |

|  | | | | | | | | | | 650 | | | | | | | | | 660 | |
|---|---|---|---|---|---|---|---|---|---|---|---|---|---|---|---|---|---|---|---|---|
| hGPRC6A | L | N | F | A | S | T | F | F | I | G | E | P | Q | D | F | T | C | K | T | R | Q |
| cGPRC6A | V | L | N | F | A | S | T | G | F | F | I | G | E | P | Q | D | F | T | C | K | T | R | Q |
| fGPRC6A | L | N | F | A | S | T | F | F | I | G | E | P | Q | D | F | T | C | K | T | R | Q |

|  | | | | | | | | | | 730 | | | | | | | | | 740 | |
|---|---|---|---|---|---|---|---|---|---|---|---|---|---|---|---|---|---|---|---|---|
| hGPRC6A | W | L | I | F | A | A | P | V | E | V | N | V | S | L | P | R | V | I | L | E |
| cGPRC6A | W | L | I | F | A | A | P | V | E | N | V | S | L | P | R | V | I | L | E |
| fGPRC6A | W | L | I | F | A | A | P | V | E | N | V | S | L | P | R | V | I | I | L | E |

|  | | | | | | | | | | 810 | | | | | | | | | 820 | |
|---|---|---|---|---|---|---|---|---|---|---|---|---|---|---|---|---|---|---|---|---|
| hGPRC6A | P | Y | A | T | T | F | G | K | Y | V | P | A | V | E | I | V | L | I | S |
| cGPRC6A | P | Y | A | T | T | F | G | K | Y | L | P | A | V | E | I | V | L | I | S |
| fGPRC6A | P | Y | A | T | T | F | G | K | Y | L | P | A | V | E | I | V | L | I | S |

|  | | | | | | | | | | 890 | | | | | | | | | 900 | |
|---|---|---|---|---|---|---|---|---|---|---|---|---|---|---|---|---|---|---|---|---|
| hGPRC6A | T | T | N | P | S | S | G | K | A | W | Q | S | D | L | A | Q |
| cGPRC6A | T | T | N | P | S | S | G | A | W | Q | S | K | D | A | Q |
| fGPRC6A | T | A | T | N | P | S | S | G | P | A | W | Q | S | R | D | A | Q |

```
         60              70              80
  PRRP  IQ CVGFE IS  FLQTLAM HS
  PRRP IQK CVGFE IS  FLQTLAM HS
  PRRP IQK CVGFE IS  FLQTLAM HS
         140             150             160
 SSYMPRVKAV IG GYSE ITMAVSRMLN
 SSYMPRVKAV IG GYSE ITMAVSRMLN
 SSYMPRVKAV IG GYSE ITMAVSRMLN
         220             230             240
 I TDDDYGR ALNTF  Q  ANNVC A
 I TDDDYGR ALNTF V Q  ANNVC A
 I TDDDYGR ALNTF V Q   ANNVC A
         300             310             320
 N NK W ASDNWS ATK TT PNVK
 N NK W ASDNWS ATK TT PNVK
 N NK W ASDNWS ATK TT PNVK
         380             390             400
 QC    S  TLAY NK  ERNF  RN
 QC    S  TLAY NK  ERNF  RN
 QC    S  TLAY NK  ERNF  RN
         460             470             480
 TFTD  NSFHFDAHGD NTGYDVV LWK
 TFTD  NSFHFDAHGD NTGYDVV LWK
 TFTD  NSFHFDAHGD NTGYDVV LWK
         540             550             560
 TTRSQH CCYEC  CPENHY NQTDM
 TTRSQH CCYEC V CPENHY NQTDM
 TTRSQH CCYEC V CPENHY NQTDM
         620             630             640
 I FTRNLNTP VKSSGGL VCYV LLCH
 I FTRNLNTP VKSSGGL VCYV LLCH
 I FTRNLNTP VKSSGGL VCYV LLCH
         700             710             720
 LQ FLKCLY P    F CTG QV CT
 LQ FLKCLY P    F CTG QV CT
 LQ FLKCLY P    F CTG QV CT
         780             790             800
    E YNEAKF TFGML YF AW TF
  LPE YNEAKF TFGML YF AW TF
  LPE YNEAKF TFGML YF AW TF
         860             870             880
 M YSYSSH SS A S SLDS
 M YSYSSH SS A S SLDS
 M YSYSSH SS A S SLDS
         940             950             960
```

FIG. 3 (Continued)

Figure 9C
FLUO-4 AM
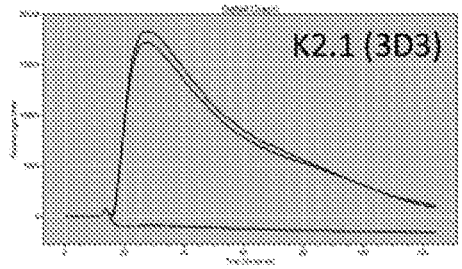 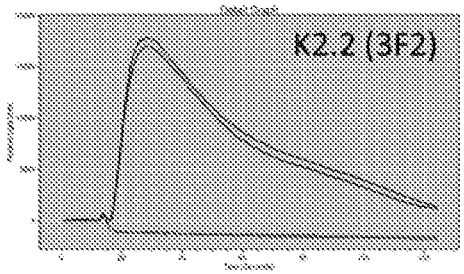
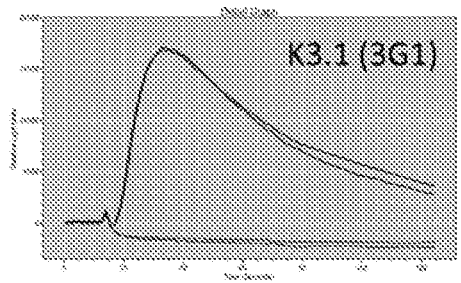 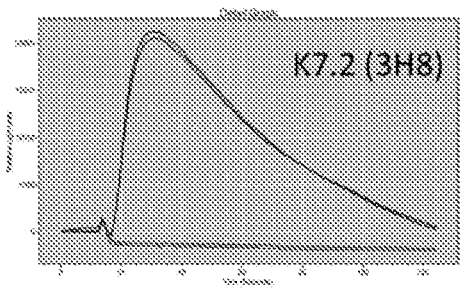
PHOTOPROTEIN (natClytin)
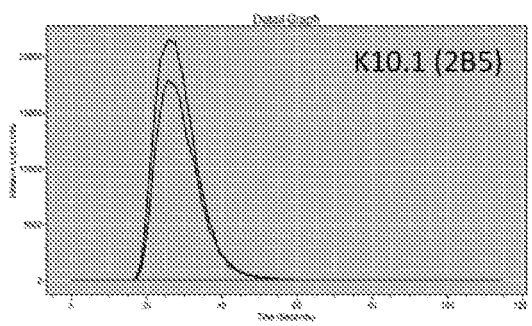 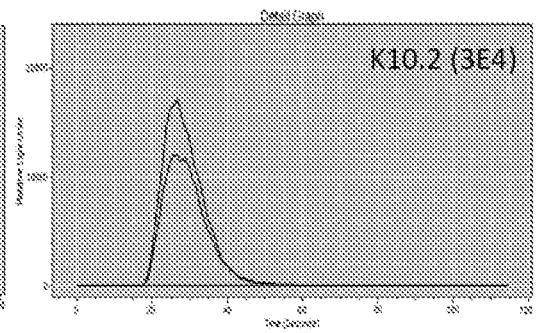
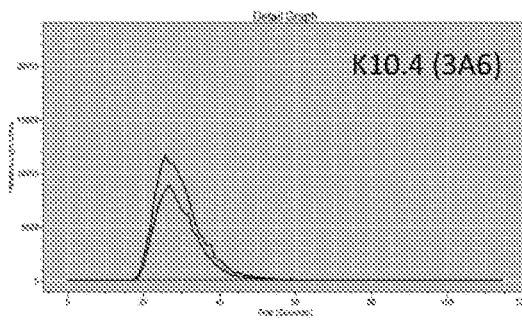 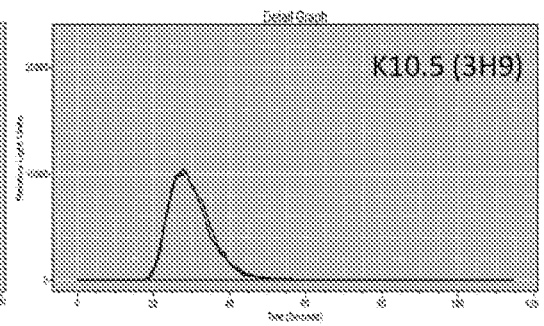

ANOVA Table for Fixed Effects

| Factor | Degrees of Freedom | | F-value | P-value |
|---|---|---|---|---|
| | Numerator | Denominator | | |
| Product Difference | 1 | 22 | 3.06 | 0.0941 |

Table of Mean Product Difference, Standard Error & 95% Confidence Intervals

| Product Difference | Mean | Standard Error | 95% Confidence Interval | |
|---|---|---|---|---|
| | | | Lower | Upper |
| Water - L-ornithine HCl | -15.28 | 8.73 | -33.40 | 2.83 |

SCREENING METHODS USING GPRC6A TASTE RECEPTORS AND PET FOOD PRODUCTS AND COMPOSITIONS PREPARED USING THE SAME

CROSS REFERENCE TO RELATED APPLICATION

This application is a national stage application filed under 35 U.S.C. § 371 of International Application No. PCT/US2019/037097 filed on Jun. 13, 2019, which claims the benefit of priority of U.S. Provisional Patent Application No. 62/685,813 filed Jun. 15, 2018, for which the entire contents of each are hereby incorporated by reference in their entirety.

SEQUENCE LISTINGS

The specification further incorporates by reference the Sequence Listing submitted herewith via EFS on Jun. 21, 2021. Pursuant to 37 C.F.R. § 1.52(e)(5), the Sequence Listing text file, identified as 0692690459SL.txt, is 36,119 bytes and was created on Jun. 21, 2021. The Sequence Listing, electronically filed herewith, does not extend beyond the scope of the specification and thus does not contain new matter.

FIELD

The presently disclosed subject matter relates to the use of GPRC6A taste receptors (e.g., a feline GPRC6A receptor) for the identification of taste modulators. The presently disclosed subject matter further relates to the use of GPRC6A taste receptors to screen pet food products and raw materials for making the same.

BACKGROUND

Taste profiles for edible compositions include basic tastes such as sweet, salt, bitter, sour, umami and kokumi. Taste profiles have also been described as including free fatty acid tastes. Chemical compounds that elicit these tastes are often referred to as tastants. Without being bound by theory, it is hypothesized that tastants are sensed by taste receptors in the mouth and throat which transmit signals to the brain where the tastants and resulting taste profiles are registered.

Pet food manufacturers have a long-standing desire to provide pet food products that have high nutritional value. In addition, and with particular regard to cat and dog foods, pet food manufacturers desire a high degree of palatability so that pets can receive the full nutritional benefit from their food. Domestic animals are notoriously finicky in their food preferences, and often refuse to eat a pet food product that it has accepted over time or refuse to eat any more than a minimal amount of a pet food product. This phenomenon may be, in part, due to the subtle differences in the sensory profiles of the raw material, which can be perceived by the domestic animals because of their gustatory and olfactory systems. As a result, pet owners frequently change types and brands of pet food in order to maintain their pets in a healthy and contented condition.

While there have been recent advances in taste and flavor technologies, there remains a need for methods of screening raw materials that are used to make pet food product, and for screening finished pet food products, to ensure that the most palatable products and processes for making the pet food products are used. There also remains a need for compounds that can enhance or modify the palatability of pet food products by enhancing or modifying the taste, texture and/or flavor profiles of the pet food products. The enhancement or modification can be used to increase the intensity of a desirable attribute, to replace a desirable attribute that is not present or somehow lost in the pet food product, or to decrease the intensity of an undesirable attribute. Similarly, there is a need to increase the acceptance of pet medications by enhancing or modifying the palatability of the medications.

Therefore, there remains a need in the art for methods to screen raw pet food materials (e.g. new protein sources), as well as final pet food products, to provide palatable and nutritious pet food. There also remains a need to identify compounds that enhance, decrease, or otherwise modulate the palatability of pet food products, or objects, and for flavor compositions comprising these compounds.

SUMMARY OF THE INVENTION

The presently disclosed subject matter provides methods for identifying compounds that enhance, increase, decrease and/or modulate the activity and/or expression of a GPRC6A receptor. In certain embodiments, the method comprising (a) contacting a test agent with a polypeptide comprising a GPRC6A receptor or a functional fragment thereof, (b) measuring a biological activity of the polypeptide, and (c) selecting as the compound, a test agent that increases or decreases the activity of the polypeptide.

The presently disclosed subject matter further provides methods for identifying a compound that modulates the activity of a GPRC6A receptor comprising (a) contacting a GPRC6A receptor agonist with a polypeptide comprising a GPRC6A receptor or a functional fragment thereof, (b) measuring a first biological activity of the polypeptide, (c) contacting a test agent with the polypeptide, (d) measuring a second biological activity of the polypeptide, and (e) selecting the test agent as the compound when the first biological activity is higher or lower than the second biological activity.

In certain embodiments, step (c) comprises selecting as the compound, a test agent that decreases the activity of the polypeptide. In certain embodiments, step (c) comprises selecting as the compound, a test agent that increases the activity of the polypeptide.

The presently disclosed subject matter further provides methods for increasing palatability of a pet foodstuff comprising: (a) contacting a polypeptide with a compound, wherein the polypeptide comprises a GPRC6A receptor or a functional fragment thereof, (b) measuring a biological activity of the polypeptide in the absence and in the presence of the compound, and (c) admixing the compound or a composition comprising the compound with a pet foodstuff, when there is a difference between the biological activity in the absence, compared to the presence of the compound.

The presently disclosed subject matter further provides methods for increasing palatability of a pet foodstuff comprising: admixing a compound or a composition comprising the compound with a pet foodstuff, wherein the compound, when brought to contact with a polypeptide comprising a GPRC6A receptor or a functional fragment thereof, is capable of increasing a biological activity of the polypeptide.

The presently disclosed subject matter also provides compositions comprising a compound, when brought to contact with a polypeptide comprising a GPRC6A receptor or a functional fragment thereof, is capable of increasing or decreasing a biological activity of a polypeptide comprising a GPRC6A receptor or a functional fragment thereof.

The presently disclosed subject matter further provides compositions comprising a compound that is capable of increasing or decreasing a biological activity of a GPRC6A receptor, wherein the compound is identified according to any method disclosed herein.

In certain embodiments, the compound is present at a concentration of between 0.0001% and 2% in the pet foodstuff. In certain embodiments, the compound is present at a concentration of between 0.001% and 2% in the pet foodstuff. In certain embodiments, the compound is present at a concentration of between 0.01% and 2% in the pet foodstuff.

The presently disclosed subject matter further provides in silico methods for identifying a compound that modulates the activity of a GPRC6A receptor comprising (a) contacting a test agent with a polypeptide comprising a GPRC6A receptor or a functional fragment thereof, (b) detecting an interaction between the test agent and one or more amino acid residue of the polypeptide, and (c) selecting as the compound, a test agent that interacts with one or more of the amino acids. In certain embodiments, the method comprises detecting an interaction between the test agent and one or more amino acids in the Venus flytrap domain (VFT) or 7 trans-membrane domain (7TM) domain of the polypeptide. In certain embodiments, the method further comprises measuring a biological activity of the polypeptide.

In certain embodiments, the GPRC6A receptor is a feline GPRC6A receptor comprising an amino acid sequence set forth in SEQ ID NO:4. In certain embodiments, a method disclosed herein further comprising detecting an in silico interaction between the test agent and one or more amino acid residue in the Venus flytrap domain (VFT), wherein the one or more amino acid residue is selected from the group consisting of Ser149, Glu170, Thr172, Tyr220, Arg279, Asp303, Asn304, Asn400 and any combination thereof. In certain embodiments, a method disclosed herein further comprising detecting an in silico interaction between the test agent and one or more amino acid residue in the seven transmembrane domain (7TM), wherein the one or more amino acid residue is selected from the group consisting of Arg662, Gln663, Phe666, Gly667, Phe670, Gln715, Glu746, Ala751, Phe752, Met755, Leu756, Ile759, Tyr793, Trp797, Phe800, Tyr804, Glu816, Val819, Ile820 and any combination thereof.

In certain embodiments, the GPRC6A receptor is a canine GPRC6A receptor comprising an amino acid sequence set forth in SEQ ID NO:5.

In certain embodiments, the compound has an EC50 value of no more than 50 mM in connection with a biological activity of the polypeptide.

In certain embodiments, the polypeptide is expressed by a cell, and wherein the test agent is contacted to the cell. In certain embodiments, the cell expresses a calcium-binding photoprotein. In certain embodiments, the cell expresses an exogenous G-protein. In certain embodiments, the polypeptide is expressed by a vector. In certain embodiments, the biological activity of the polypeptide is measured by monitoring a calcium concentration or a cGMP activity within the cell. In certain embodiments, the calcium concentration is monitored by fluorescence detection or luminescence detection. In certain embodiments, the fluorescence detection comprises a calcium sensitive fluorescent dye.

In certain embodiments, any method disclosed herein can further comprises testing the compound in an animal feeding test.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

BRIEF DESCRIPTION OF THE DRAWINGS

FIG. 1 depicts feline, canine and human GPRC6A receptor nucleotide sequences (SEQ ID NOs: 1-3) along with the corresponding amino acid sequences (SEQ ID NOs: 4-6), respectively.

Figure 3:
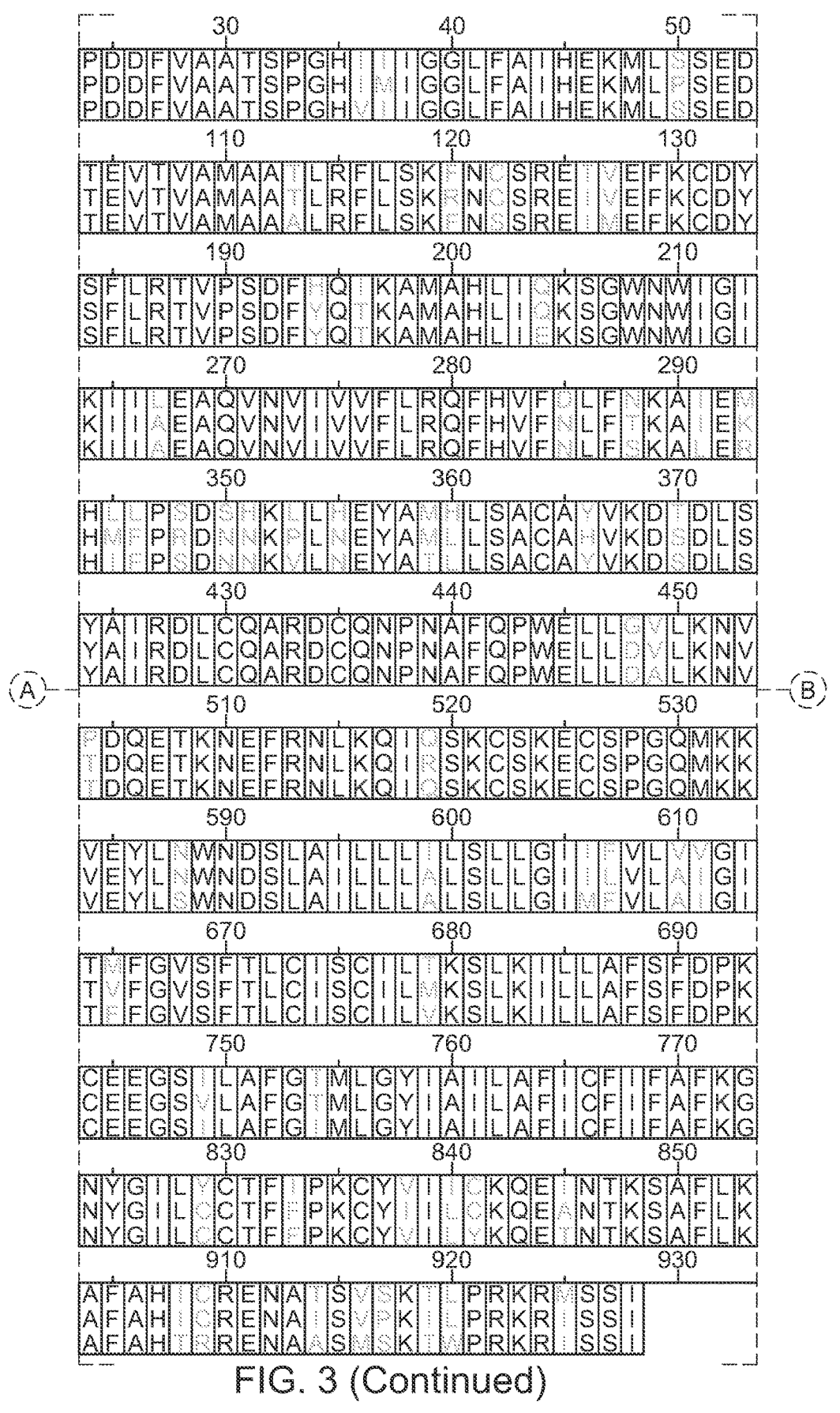

FIG. 3 depicts an alignment of human, canine, and feline GPRC6A. Alignments were performed in Discovery Studio.

FIG. 5A depicts an overview of the flytrap domain of fGPR6A indicating where L-lysine binds between the flytrap's upper lobe (above in the figure) and the lower lobe (below in the figure). FIG. 5B depicts a close-up of the binding mode of L-lysine to fGPR6A. L-lysine can make hydrogen bonds to Ser149, Glu170, Thr172, Arg279 and Asn400. The charged nitrogen atoms of lysine can form charged interactions with Asp303 and Glu170.

FIG. 6A depicts an overview of the flytrap domain of fGPR6A indicating where L-arginine binds between the flytrap's upper lobe (above in the figure) and the lower lobe (below in the figure). FIG. 6B depicts a close-up of the binding mode of L-arginine. L-arginine can make hydrogen bonds to Ser149, Glu170, Thr172, Arg279 and Asn400. The charged nitrogen atoms of arginine can make charged interactions with Asp303 and Glu170.

FIG. 7A depicts an overview of the 7TM domain of fGPR6A indicating where testosterone binds. FIG. 7B depicts a close-up of the binding mode testosterone. The transmembrane active site includes residues Arg662, Gln663, Phe666, Gly667, and Phe670 on helix 3, Gln715 on helix 4, Glu746 on EC2, Ala751, Phe752, Met755, Leu756 and Ile759 on helix 5, Tyr793, Trp797, Phe800 and Tyr804 on helix 6, and Glu816, Val819 and Ile820 on helix 7. Helix numbering is as per the helix plot shown in the figure above. Note that not all residues listed are shown in the right-hand figure for brevity. Possible hydrogen bonds are shown to Arg662 and to Tyr793.

FIG. 8A depicts an overview of the 7TM domain of fGPR6A indicating where Calindol binds. FIG. 8B depicts a close-up of the binding mode of Calindol. The 7TM active site is as described in the previous figure. Potential hydrogen bonds from Calindol to Glu816 are shown.

FIGS. 9A-9C depict characterization of a cell line clone with various test compounds. FIG. 9A depicts specific response to L-amino acids with induction of gene expression. FIG. 9B depicts negative response to test compounds without induction of gene expression. FIG. 9C depicts examples of kinetic fluorescent/luminescent traces obtained at FLIPRR Tetra The receptor was not activated by magnesium ion alone.

DETAILED DESCRIPTION

Figure 2:
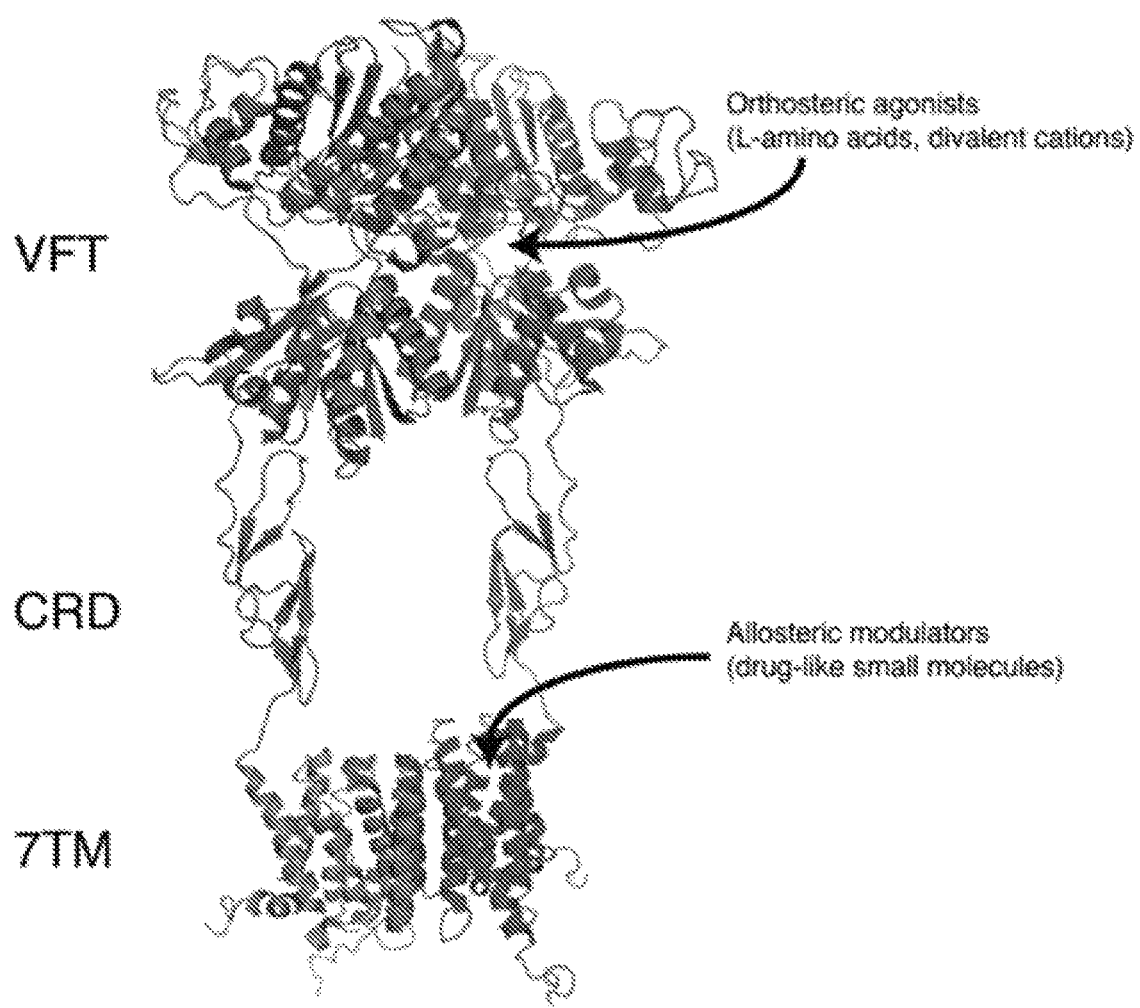
FIG. 2 depicts a schematic structure of a GPRC6A homodimer. Each monomer contains three principal domains: an extracellular Venus flytrap domain (VFT) that binds orthosteric agonists to initiate a signal; a seven-helical transmembrane domain (7TM) that transmits this signal to the cell interior; and a cysteine-rich domain (CRD) domain that connects the two. Certain Class C GPCRs modulators can trigger the receptor by binding to the 7TM domain.
Figure 4:
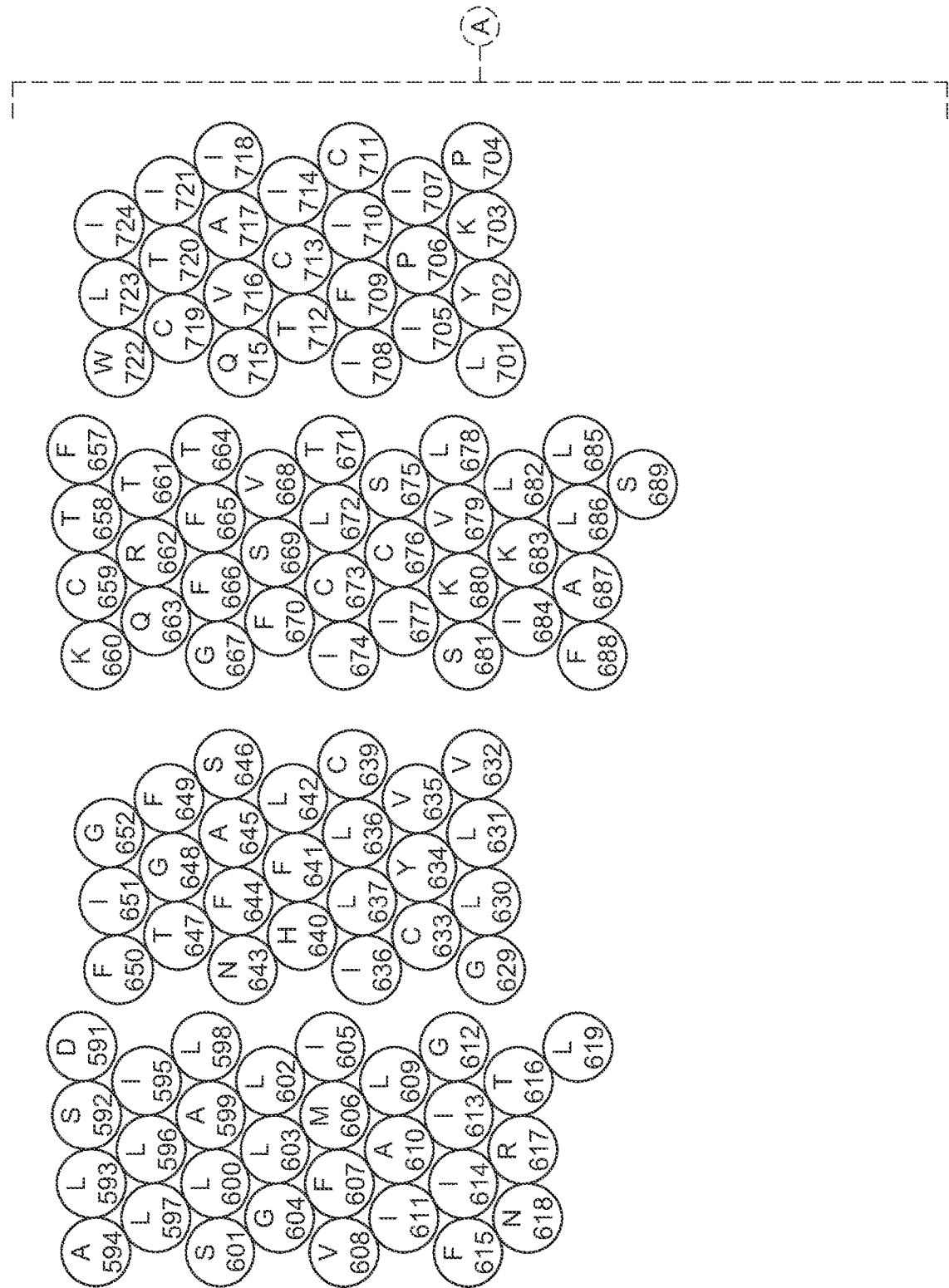
FIG. 4 depicts a helix plot of the 7TM (seven transmembrane) domain of GPRC6A. Helices are numbered 1 to 7 from the bottom of the picture to the top (N-terminus to C-terminus). An $8^{th}$ C-terminal helix is also shown in the figure.
Figure 4:
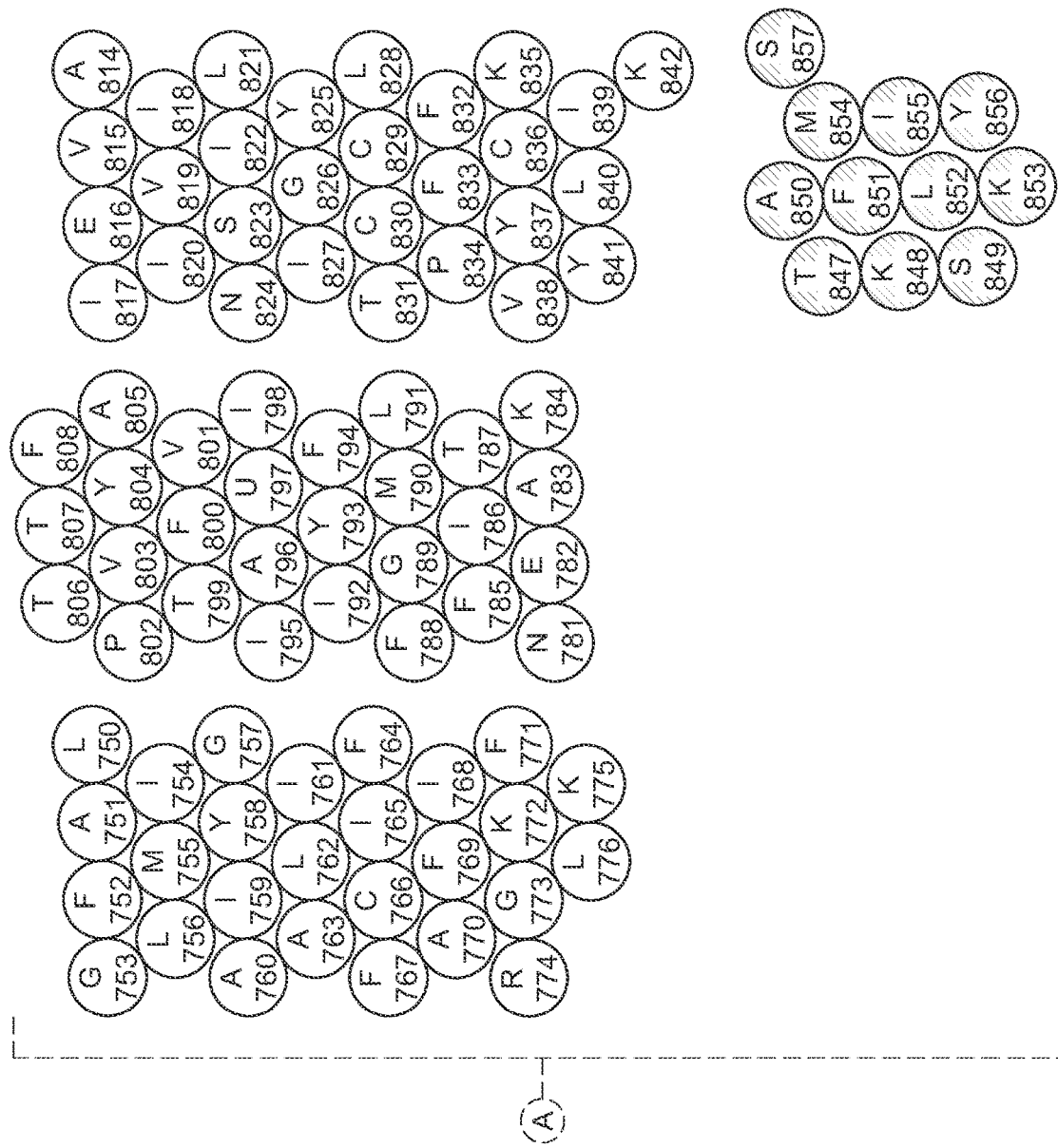
Figure 5A:
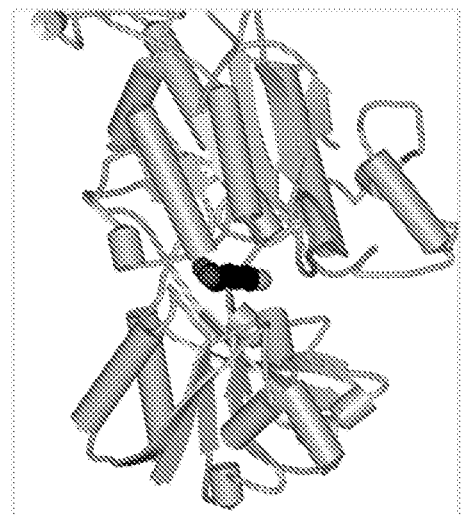
FIGS. 5A-5B depict a L-lysine molecule bound to fGPR6A.
Figure 5B:
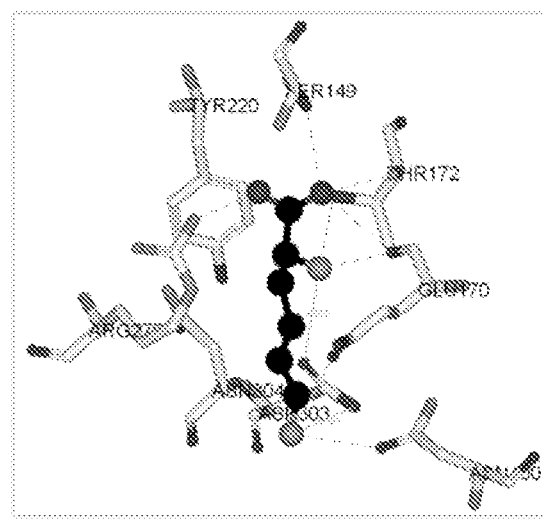
Figure 6A:
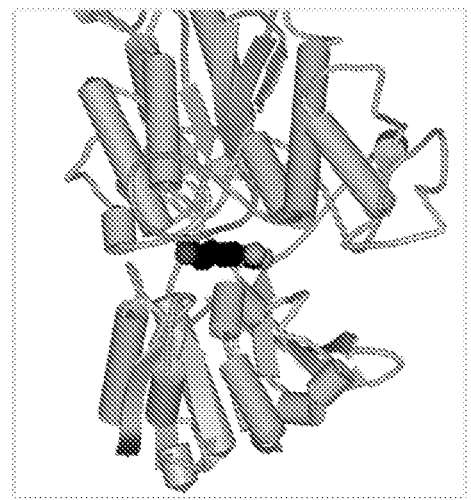
FIGS. 6A-6B depict a L-arginine molecule bound to fGPR6A.
Figure 6B:
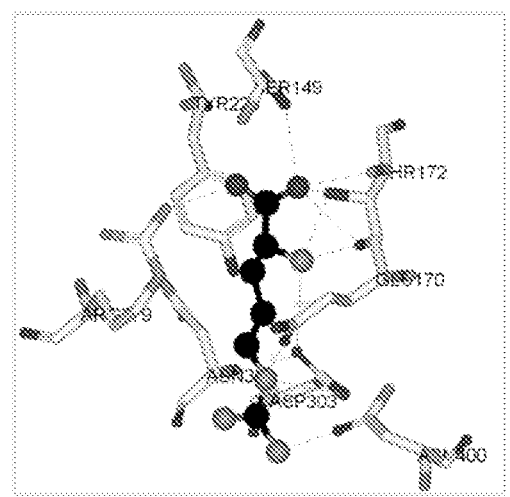
Figure 7A:
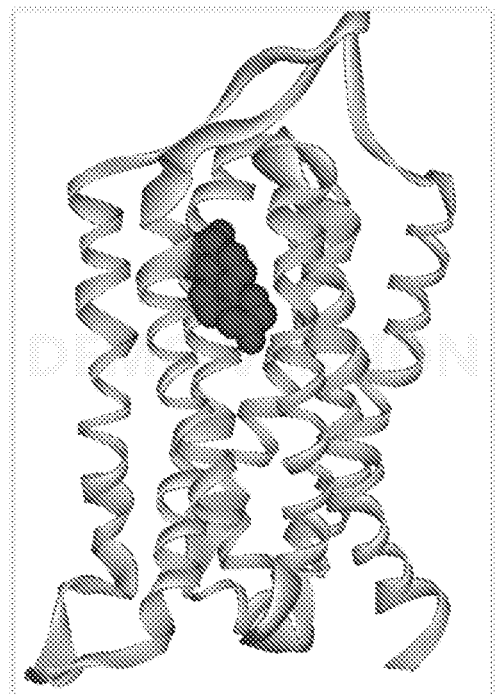
FIGS. 7A-7B depict a testosterone molecule bound to the 7TM transmembrane domain of fGPRC6A. Testosterone is a known agonist to human GPRC6A.
Figure 7B:
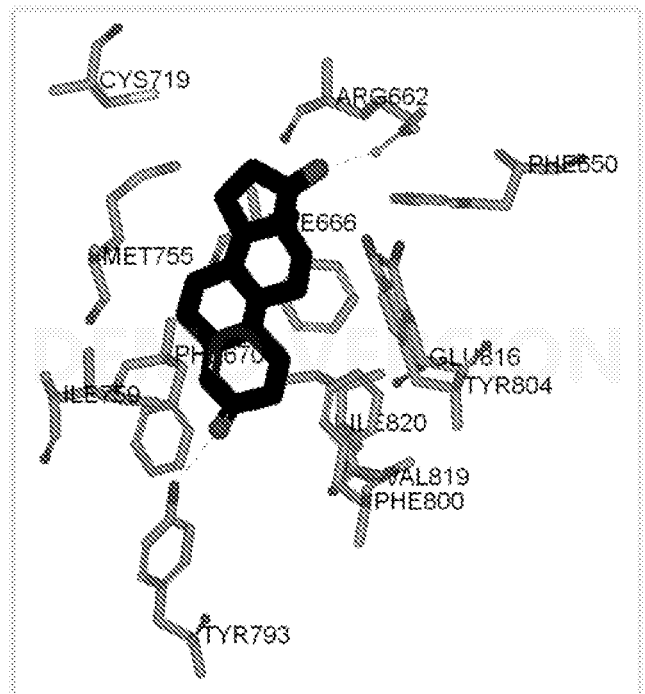
Figure 8A:
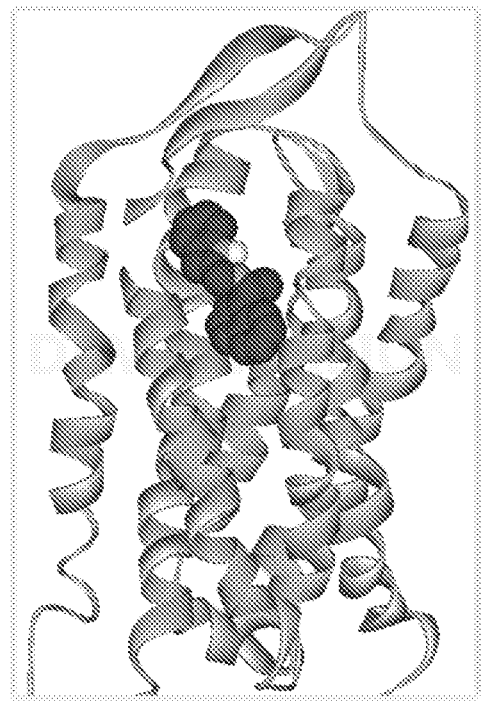
FIGS. 8A-8B depict a Calindol molecule bound to the 7TM transmembrane domain of fGPRC6A. Calindol is a known antagonist to human GPRC6A.
Figure 8B:
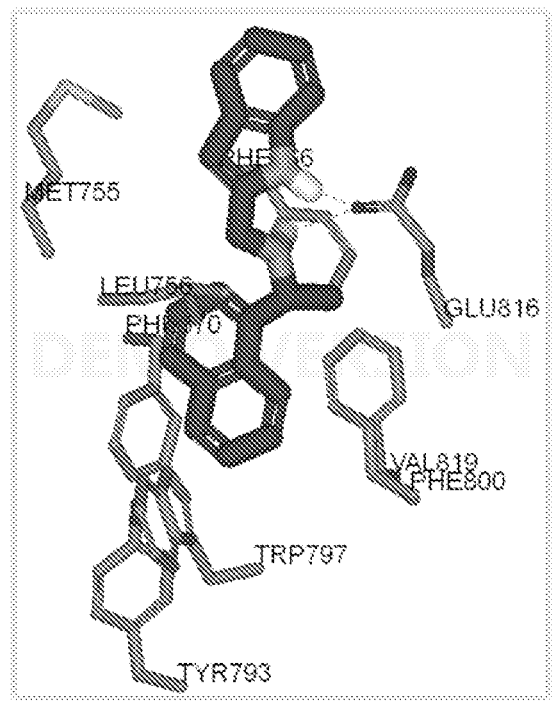

The presently disclosed subject matter relates to methods for screening and identifying compounds that modulate the activity and/or expression of GPRC6A receptors. The presently disclosed subject matter further relates to making palatable, nutritionally-complete pet food products and medicines, wherein the raw materials of the pet food and/or finalized pet food product or medicine is screened to determine if it contains compounds that modulate the GPRC6A receptors. Furthermore, such screening methods can be used to select raw materials and/or finalized pet food products that comprise GPRC6A receptor activating compounds.

Compounds identified through said methods can be used to modify the palatability of pet food products and medicines by increasing or decreasing a taste, e.g., an umami taste and/or a kokumi taste. Said compounds can also be used to increase an umami taste and/or a kokumi taste of an animal, e.g., a cat, and thereby increase palatability and ingestion by the animal.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the methods and compositions of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "taste" refers to a sensation caused by activation of receptor cells in a subject's taste buds. In certain embodiments, taste can be selected from the group consisting of sweet, sour, salt, bitter, kokumi and umami. In certain embodiments, "taste" can include free fatty acid taste. See, e.g., Cartoni et al., J. of Neuroscience, 30(25): 8376-8382 (2010), the contents of which are incorporated herein by reference. In certain embodiments, a taste is elicited in a subject by a "tastant." In certain embodiments, a tastant can be a synthetic tastant. In certain embodiments, the tastant is obtained or prepared from a natural source.

As used herein, "taste profile" refers to a combination of tastes, such as, for example, one or more of a sweet, sour, salt, bitter, umami, kokumi and free fatty acid taste. In certain embodiments, a taste profile is produced by one or more tastant that is present in a composition at the same or different concentrations. In certain embodiments, a taste profile refers to the intensity of a taste or combination of tastes, for example, a sweet, sour, salt, bitter, umami, kokumi and free fatty acid taste, as detected by a subject or any assay known in the art. In certain embodiments, modifying, changing or varying the combination of tastants in a taste profile can change the sensory experience of a subject.

As used herein, "flavor" refers to one or more sensory stimuli, such as, for example, one or more of taste (gustatory), smell (olfactory), touch (tactile) and temperature (thermal) stimuli. In certain non-limiting embodiments, the sensory experience of a subject exposed to a flavor can be classified as a characteristic experience for the particular flavor. For example, a flavor can be identified by the subject as being, but not limited to, a floral, citrus, berry, nutty, caramel, chocolate, peppery, smoky, cheesy, meaty, etc., flavor. As used herein, a flavor composition can be selected from a liquid, solution, dry powder, spray, paste, suspension and any combination thereof. The flavor can be a natural composition, an artificial composition, a nature identical, or any combination thereof.

As used herein, "flavor profile" refers to a combination of sensory stimuli, for example, tastes, such as sweet, sour, bitter, salty, umami, kokumi and free fatty acid tastes, and/or olfactory, tactile and/or thermal stimuli. In certain embodiments, the flavor profile comprises one or more flavors which contribute to the sensory experience of a subject. In certain embodiments, modifying, changing or varying the combination of stimuli in a flavor profile can change the sensory experience of a subject.

As used herein "admixing," for example, "admixing the flavor composition or combinations thereof of the present application with a food product," refers to the process where the flavor composition, or individual components of the flavor composition, is mixed with or added to the completed product or mixed with some or all of the components of the product during product formation or some combination of these steps. When used in the context of admixing, the term "product" refers to the product or any of its components. This admixing step can include a process selected from the step of adding the flavor composition to the product, spraying the flavor composition on the product, coating the flavor composition on the product, suspending the product in the flavor composition, painting the flavor composition on the product, pasting the flavor composition on the product, encapsulating the product with the flavor composition, mixing the flavor composition with the product and any combination thereof. The flavor composition can be a solution, liquid, dry powder, spray, paste, suspension and any combination thereof.

As used herein, "palatability" can refer to the overall willingness of a human or non-human animal, for example, a companion animal, to eat a certain food product. Increasing the "palatability" of a food product can lead to an increase in the enjoyment and acceptance of the food by the human or non-human animal to ensure the human or non-human animal eats a "healthy amount" of the food. Decreasing the "palatability" of a food product can lead to a decrease in the enjoyment and acceptance of the food by the human or non-human animal. The term "healthy amount" of a food as used herein refers to an amount that enables the human or non-human animal to maintain or achieve an intake contributing to its overall general health in terms of micronutrients, macronutrients and calories, for example, such as set out in the "Mars Petcare Essential Nutrient Standards." In certain embodiments, "palatability" can mean a relative preference of a human or non-human animal for one food product over another. For example, when a human or non-human animal shows a preference for one of two or more food products, the preferred food product is more "palatable," and has "enhanced palatability." In certain embodiments, the relative palatability of one food product compared to one or more other food products can be determined, for example, in side-by-side, free-choice comparisons, e.g., by relative consumption of the food products, or other appropriate measures of preference indicative of palatability. Palatability can be determined by a standard testing protocol in which the animal has equal access to both food products such as a test called "two-bowl test" or "versus test." Such preference can arise from any of the animal's senses, but can be related to, inter alia, taste, aftertaste, smell, mouth feel and/or texture.

The term "pet food" or "pet food product" or "final pet food product" means a product or composition that is intended for consumption by a companion animal, such as cats, dogs, guinea pigs, rabbits, birds and horses. For example, but not by way of limitation, the companion animal can be a "domestic" dog, e.g., *Canis lupus familiaris*. In certain embodiments, the companion animal can be a "domestic" cat such as *Felis domesticus*. A "pet food" or "pet food product" includes any food, feed, snack, food supplement, liquid, beverage, treat, toy (chewable and/or consumable toys), meal substitute or meal replacement.

The term "human food" or "human food product" or "final human food product" means a product or composition that is intended for consumption by a human. A "human food" or "human food product" includes any food, feed, snack, food supplement, liquid, beverage, treat, meal substitute or meal replacement.

In certain embodiments, a "food product" includes human and/or pet food products. As used herein "nutritionally-complete" refers to pet food product that contains all known required nutrients for the intended recipient of the pet food product, in appropriate amounts and proportions based, for example, on recommendations of recognized or competent authorities in the field of companion animal nutrition. Such foods are therefore capable of serving as a sole source of dietary intake to maintain life, without the addition of supplemental nutritional sources.

The term "raw material" means a plant and/or animal material before being processed or manufactured into a final pet food product. In certain embodiments, a "raw material" is not significantly processed in order to separate it into individual elements prior to analysis (e.g., by extraction, purification, fractionation and/or concentration). A "raw material" includes a protein source for a pet food product. In certain embodiments, the raw material is a novel protein source that does not compete with the human food sources (i.e., a protein source that is not commonly eaten by humans). In certain embodiments, the raw material is a by-product of the human food chain. In certain non-limiting embodiments, the "raw material" is processed, for example, in order to separate it into individual elements prior to analysis (e.g., by extraction, purification, fractionation and/or concentration), prior to being analyzed according to the methods described herein.

As used herein "flavor composition" refers to at least one compound or biologically acceptable salt thereof that modulates, including enhancing, multiplying, potentiating, decreasing, suppressing, or inducing, the tastes, smells, flavors and/or textures of a natural or synthetic tastant, flavoring agent, taste profile, flavor profile and/or texture profile in an animal or a human. In certain embodiments, the flavor composition comprises a combination of compounds or biologically acceptable salts thereof. In certain embodiments, the flavor composition includes one or more excipients.

As used herein, the terms "modulates" or "modifies" refers to an increase or decrease in the amount, quality or effect of a particular activity of a receptor and/or an increase or decrease in the expression, activity or function of a receptor. "Modulators," as used herein, refer to any inhibitory or activating compounds identified using in silico, in vitro and/or in vivo assays for, e.g., agonists, antagonists, allosteric modulators and their homologs, including fragments, variants and mimetics.

"Inhibitors" or "antagonists," as used herein, refer to modulating compounds that reduce, decrease, block, prevent, delay activation, inactivate, desensitize or down regulate the biological activity and/or expression of a receptor or pathway of interest. The term "antagonist" includes full, partial, and neutral antagonists as well as inverse agonists.

"Inducers," "activators" or "agonists," as used herein, refer to modulating compounds that increase, induce, stimulate, open, activate, facilitate, enhance activation, sensitize or upregulate a receptor or pathway of interest. The term "agonist" includes full and partial agonists.

"Allosteric modulators" as used herein, refer to "positive allosteric modulators" and "negative allosteric modulators." "Positive allosteric modulators" refer to modulating compounds that increase, induce, stimulate, open, activate, facilitate, enhance activation, sensitize or up regulate a receptor or pathway of interest caused by the binding of a different compound to the receptor. "Negative allosteric modulators" refer to modulating compounds that reduce, decrease, block, prevent, delay activation, inactivate, desensitize or down regulate the biological activity and/or expression of a receptor or pathway of interest caused by the binding of a different compound to the receptor.

As used herein, the terms "vector" and "expression vector" refer to DNA molecules that are either linear or circular, into which another DNA sequence fragment of appropriate size can be integrated. Such DNA fragment(s) can include additional segments that provide for transcription of a gene encoded by the DNA sequence fragment. The additional segments can include and are not limited to: promoters, transcription terminators, enhancers, internal ribosome entry sites, untranslated regions, polyadenylation signals, selectable markers, origins of replication and such like. Expression vectors are often derived from plasmids, cosmids, viral vectors and yeast artificial chromosomes. Vectors are often recombinant molecules containing DNA sequences from several sources.

The term "nucleic acid molecule" and "nucleotide sequence," as used herein, refers to a single or double stranded covalently-linked sequence of nucleotides in which the 3' and 5' ends on each nucleotide are joined by phosphodiester bonds. The nucleic acid molecule can include deoxyribonucleotide bases or ribonucleotide bases, and can be manufactured synthetically in vitro or isolated from natural sources.

The terms "polypeptide," "peptide," "amino acid sequence" and "protein," used interchangeably herein, refer to a molecule formed from the linking of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis or enzymatic synthesis. The terms can apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid," as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate and O-phosphoserine. Amino acid analogs and derivatives can refer to compounds that have the same basic chemical structure as a naturally occurring amino acid, i.e., a carbon that is bound to a hydrogen, a carboxyl group, an amino group and an R group, e.g., homoserine, norleucine, methionine sulfoxide and methionine methyl sulfonium. Such analogs can have modified R groups (e.g., norleucine) or modified peptide backbones, but retain the same basic chemical structure as a naturally occurring amino acid. Amino acid mimetics means chemical compounds that have a structure that is different from the general chemical structure of an amino acid, but that function in a manner similar to a naturally occurring amino acid.

The terms "isolated" or "purified", used interchangeably herein, refers to a nucleic acid, a polypeptide, or other biological moiety that is removed from components with which it is naturally associated. The term "isolated" can refer to a polypeptide that is separate and discrete from the whole organism with which the molecule is found in nature or is present in the substantial absence of other biological macromolecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome.

As used herein, the term "recombinant" can be used to describe a nucleic acid molecule and refers to a polynucleotide of genomic, RNA, DNA, cDNA, viral, semisynthetic or synthetic origin which, by virtue of its origin or manipulation is not associated with all or a portion of the polynucleotide with which it is associated in nature.

The term "fusion," as used herein, refers to joining of different peptide or protein segments by genetic or chemical methods wherein the joined ends of the peptide or protein segments may be directly adjacent to each other or may be separated by linker or spacer moieties such as amino acid residues or other linking groups.

2. GPRC6A Receptors

The presently disclosed subject matter provides GPRC6A receptors for use in the disclosed methods. The GPRC6A receptors of the present disclosure can include mammalian GPRC6A receptors such as, but not limited to, a feline GPRC6A receptor (fGPRC6A), a canine GPRC6A (cGPRC6A) and a human GPRC6A (hGPRC6A).

In certain non-limiting embodiments, the GPRC6A receptor is a feline GPRC6A receptor.

In certain embodiments, a GPRC6A receptor for use in the presently disclosed methods encompasses a feline GPRC6A taste receptor having the nucleotide sequence set forth in SEQ ID NO:1, and/or the amino acid sequence set forth in SEQ ID NO: 4, including fragments thereof (e.g., functional fragments thereof) and variants thereof. fGPRC6A residues contributing to the Venus flytrap ligand binding site include, but are not limited to, Ser149, Glu170, Thr172, Tyr220, Arg279, Asp303, Asn304 and Asn400. In addition, it is known from other Class C GPCRs that ligands can also activate the receptors by binding to their 7TM transmembrane domains. fGPRC6A residues comprising the 7TM ligand binding site include, but are not limited to, Arg662, Gln663, Phe666, Gly667, Phe670, Gln715, Glu746, Ala751, Phe752, Met755, Leu756, Ile759, Tyr793, Trp797, Phe800, Tyr804, Glu816, Val819 and Ile820.

In certain embodiments, the GPRC6A receptor for use in the presently disclosed subject matter can include a receptor encoded by a nucleotide sequence that is at least 85%, at least 90%, at least 91%, at least 92%, at least 93%, at least 94%, at least 95%, at least 96%, at least 97%, at least 98% or at least 99% homologous to SEQ ID NO: 1 (homology, as that term is used herein, may be measured using standard software such as BLAST or FASTA).

In certain embodiments, the GPRC6A receptor for use in the presently disclosed methods can include a receptor comprising an amino acid sequence that is between about 33% and 99%, between about 34% and 99%, between about 35% and 99%, between about 40% and 99%, between about 45% and 99%, between about 50% and 99%, between about 55% and 99%, between about 60% and 99%, between about 61% and 99%, between about 65% and 99%, between about 70% and 99%, between about 72% and 99%, between about 75% and 99%, between about 79% and 99%, between about 80% and 99%, between about 84% and 99%, between about 85% and 99%, between about 87% and 99%, between about 89% and 99%, between about 90% and 99%, between about 95% and 99%, or between about 97% and 99% homologous to any one of SEQ ID NO: 4 (homology, as that term is used herein, may be measured using standard software such as BLAST or FASTA).

In certain embodiments, the GPRC6A receptor for use in the presently disclosed methods can include a receptor comprising an amino acid sequence that is at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% homologous to SEQ ID NO: 4 (homology, as that term is used herein, may be measured using standard software such as BLAST or FASTA).

In certain embodiments, the GPRC6A receptor is a fGPRC6A comprising an amino acid sequence as set forth in SEQ ID NO: 4, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 1, or a sequence at least 99, 98, 97, 96, 95, 90, 85 or 80 percent homologous thereto (homology, as that term is used herein, may be measured using standard software such as BLAST or FASTA).

In certain non-limiting embodiments, the GPRC6A receptor is a canine GPRC6A receptor.

In certain embodiments, a GPRC6A receptor for use in the presently disclosed methods encompasses a canine GPRC6A taste receptor having the nucleotide sequence set forth in SEQ ID NO:2, and/or the amino acid sequence set forth in SEQ ID NO: 5, including fragments thereof (e.g., functional fragments thereof) and variants thereof.

In certain embodiments, the GPRC6A receptor for use in the presently disclosed subject matter can include a receptor encoded by a nucleotide sequence that is at least 85%, at least 90%, at least 91%, at least 92%, at least 93%, at least 94%, at least 95%, at least 96%, at least 97%, at least 98% or at least 99% homologous to SEQ ID NO: 2 (homology, as that term is used herein, may be measured using standard software such as BLAST or FASTA).

In certain embodiments, the GPRC6A receptor for use in the presently disclosed methods can include a receptor comprising an amino acid sequence that is between about 33% and 99%, between about 34% and 99%, between about 35% and 99%, between about 40% and 99%, between about 45% and 99%, between about 50% and 99%, between about 55% and 99%, between about 60% and 99%, between about 61% and 99%, between about 65% and 99%, between about 70% and 99%, between about 72% and 99%, between about 75% and 99%, between about 79% and 99%, between about 80% and 99%, between about 84% and 99%, between about 85% and 99%, between about 87% and 99%, between about 89% and 99%, between about 90% and 99%, between about 95% and 99%, or between about 97% and 99% homologous to any one of SEQ ID NO: 5 (homology, as that term is used herein, may be measured using standard software such as BLAST or FASTA).

In certain embodiments, the GPRC6A receptor for use in the presently disclosed methods can include a receptor comprising an amino acid sequence that is at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% homologous to SEQ ID NO: 5 (homology, as that term is used herein, may be measured using standard software such as BLAST or FASTA).

In certain embodiments, the GPRC6A receptor comprises an amino acid sequence set forth in SEQ ID NO: 5, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 2, or a sequence at least 99, 98, 97, 96, 95, 90, 85 or 80 percent homologous thereto (homology, as that term is used herein, may be measured using standard software such as BLAST or FASTA).

In certain non-limiting embodiments, the GPRC6A receptor is a human GPRC6A receptor.

In certain embodiments, a GPRC6A receptor for use in the presently disclosed methods encompasses a human GPRC6A taste receptor having the nucleotide sequence set forth in SEQ ID NO:3, and/or the amino acid sequence set forth in SEQ ID NO: 6, including fragments thereof (e.g., functional fragments thereof) and variants thereof.

In certain embodiments, the GPRC6A receptor for use in the presently disclosed subject matter can include a receptor encoded by a nucleotide sequence that is at least 85%, at least 90%, at least 91%, at least 92%, at least 93%, at least 94%, at least 95%, at least 96%, at least 97%, at least 98% or at least 99% homologous to SEQ ID NO: 3 (homology, as that term is used herein, may be measured using standard software such as BLAST or FASTA).

In certain embodiments, the GPRC6A receptor for use in the presently disclosed methods can include a receptor comprising an amino acid sequence that is between about 33% and 99%, between about 34% and 99%, between about 35% and 99%, between about 40% and 99%, between about 45% and 99%, between about 50% and 99%, between about 55% and 99%, between about 60% and 99%, between about 61% and 99%, between about 65% and 99%, between about 70% and 99%, between about 72% and 99%, between about 75% and 99%, between about 79% and 99%, between about 80% and 99%, between about 84% and 99%, between about 85% and 99%, between about 87% and 99%, between about 89% and 99%, between about 90% and 99%, between about 95% and 99%, or between about 97% and 99% homologous to any one of SEQ ID NO: 6 (homology, as that term is used herein, may be measured using standard software such as BLAST or FASTA).

In certain embodiments, the GPRC6A receptor for use in the presently disclosed methods can include a receptor comprising an amino acid sequence that is at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% homologous to SEQ ID NO: 6 (homology, as that term is used herein, may be measured using standard software such as BLAST or FASTA).

In certain embodiments, the GPRC6A receptor comprises an amino acid sequence set forth in SEQ ID NO: 6, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 3, or a sequence at least 99, 98, 97, 96, 95, 90, 85 or 80 percent homologous thereto (homology, as that term is used herein, may be measured using standard software such as BLAST or FASTA).

In certain embodiments, the GPRC6A receptor for use in the presently disclosed methods can comprise a functional fragment of any GPRC6A receptor disclosed herein. In certain embodiments, GPRC6A is a Class C G-Protein-Coupled Receptor (GPCR) comprising three domains: a Venus flytrap domain that binds to the receptor's native ligands, a seven-helix transmembrane domain (7TM) that transmits signal to the cellular interior, and a cysteine rich domain (CRD) that connects the two. In certain embodiments, a functional fragment of fGPRC6A is selected from the group consisting of the Venus flytrap domain (amino acid residues 1-496), the Venus flytrap domain including the CRD domain (amino acid residues 1-590), the 7TM domain (amino acid residues 591-842), the 7TM domain including a C-terminus helical extension (amino acid residues 594-

857), any peptide substantially overlapping any one of the domains thereof, any variation thereof and any combination thereof.

In certain embodiments, homology is described as a percent identity between two sequences. The percent identity of two amino acid sequences or of two nucleotide sequences can be determined by aligning the sequences for optimal comparison purposes (e.g., gaps can be introduced in the first sequence for best alignment with the sequence) and comparing the amino acid residues or nucleotides at corresponding positions. The percent identity can be determined by the number of identical amino acid residues or nucleotides in the sequences being compared (e.g., % identity=number of identical positions/total number of positions×100).

The determination of percent identity between two sequences can be determined using a mathematical algorithm known to those of skill in the art. A non-limiting example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877, the disclosures of which are incorporated herein by reference in their entireties. The NBLAST and XBLAST programs of Altschul, et al. (1990) J. Mol. Biol. 215:403-410 have incorporated such an algorithm. BLAST nucleotide searches can be performed with the NBLAST program, for example, score=100, wordlength=12, to obtain nucleotide sequences homologous to nucleotide sequences of the invention. BLAST protein searches can be performed with the XBLAST program, for example, score=50, wordlength=3, to obtain amino acid sequences homologous to amino acid sequence of the invention. To obtain gapped alignments for comparison purposes, Gapped BLAST can be utilized as described in Altschul et al. (1997) Nucleic Acids Res. 25:3389-3402, the disclosure of which is incorporated herein by reference in its entirety. Alternatively, PSI-Blast can be used to perform an iterated search, which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. An additional non-limiting example of a mathematical algorithm utilized for the comparison of sequences is the algorithm of Myers and Miller, CABIOS (1989), the disclosure of which is incorporated herein by reference in its entirety. The ALIGN program (version 2.0), which is part of the CGC sequence alignment software package, has incorporated such an algorithm. Other non-limiting examples of algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8, the disclosures of which are incorporated herein by reference in their entireties. Within FASTA, ktup is a control option that sets the sensitivity and speed of the search.

In certain embodiments, the disclosed subject matter provides for the use of an isolated or purified GPRC6A receptor and/or variants and fragments thereof. The disclosed subject matter also encompasses the use of sequence variants. In certain embodiments, variation can occur in either or both the coding and non-coding regions of a nucleotide sequence of a GPRC6A receptor. Variants can include a substantially homologous protein encoded by the same genetic locus in an organism, i.e., an allelic variant. Variants also encompass proteins derived from other genetic loci in an organism, e.g., feline, but having substantial homology to the GPRC6A receptor, i.e., a homolog. Variants can also include proteins substantially homologous to the GPRC6A receptor but derived from another organism, i.e., an ortholog. Variants also include proteins that are substantially homologous to the GPRC6A receptor that are produced by chemical synthesis. Variants also include proteins that are substantially homologous to the GPRC6A receptor that are produced by recombinant methods.

Orthologs, homologs and allelic variants can be identified using methods well known in the art. These variants can include a nucleotide sequence encoding a receptor that is at least about 60-65%, about 65-70%, about 70-75, about 80-85%, about 90-95%, about 95-99% or more homologous to any one of the nucleotide sequences set forth in SEQ ID NOs: 1-3, or fragments thereof. Such nucleic acid molecules can readily be identified as being able to hybridize under stringent conditions, to any one of the nucleotide sequences set forth in SEQ ID NOs: 1-3, or a fragment thereof. In certain embodiments, two polypeptides (or regions thereof) are substantially homologous when the amino acid sequences are at least about 60-65%, about 65-70%, about 70-75, about 80-85%, about 90-95%, about 95-99% or more homologous to any one of the amino acid sequences set forth in SEQ ID NOs: 4-6, or a fragment thereof. A substantially homologous amino acid sequence, according to the disclosed subject matter, will be encoded by a nucleic acid sequence hybridizing to the nucleic acid, or portion thereof, of any one of the nucleotide sequences set forth in SEQ ID NOs: 1-3 under stringent conditions.

The GPRC6A receptors for use in the methods of the disclosed subject matter include GPRC6A receptors having additions, deletions or substitutions of amino acid residues (variants) which do not substantially alter the biological activity of the receptor. Those individual sites or regions of the GPRC6A receptors which may be altered without affecting biological activity can be determined by examination of the structure of the GPRC6A receptor extracellular domain, for example. Alternatively and/or additionally, one can empirically determine those regions of the receptor which would tolerate amino acid substitutions by alanine scanning mutagenesis (Cunningham et al., Science 244, 1081-1085 (1989), the disclosure of which is hereby incorporated by reference in its entirety). In the alanine scanning mutagenesis method, selected amino acid residues are individually substituted with a neutral amino acid (e.g., alanine) in order to determine the effects on biological activity.

It is generally recognized that conservative amino acid changes are least likely to perturb the structure and/or function of a polypeptide. Accordingly, the disclosed subject matter encompasses one or more conservative amino acid changes within a GPRC6A receptor. Conservative amino acid changes generally involve substitution of one amino acid with another that is similar in structure and/or function (e.g., amino acids with side chains similar in size, charge and shape). Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a GPRC6A receptor can be replaced with other amino acid residues from the same side chain family and the altered protein can be tested for retained function using the functional assays described herein. Modifications can be introduced into a GPRC6A receptor of the present disclosure by standard techniques known in the art, such as site-directed mutagenesis and PCR-mediated mutagenesis. If such substitutions result in a retention in biological activity, then more substantial changes can be introduced, and/or other additions/deletions may be made, and the resulting products screened. In certain embodiments, deletions or additions can be from 5-10 residues, alternatively from 2-5 amino acid residues or from 1-2 residues, and values in between.

The disclosed subject matter also provides for fusion proteins that comprise a GPRC6A receptor, or fragment thereof. In certain embodiments, the disclosed subject matter provides for fusion proteins of a GPRC6A receptor, or functional fragments thereof, and an immunoglobulin heavy chain constant region. In certain embodiments, a fusion protein of the present disclosure can include a detectable marker, a functional group such as a carrier, a label, a stabilizing sequence or a mechanism by which GPRC6A receptor agonist binding can be detected. Non-limiting embodiments of a label include a FLAG tag, a His tag, a MYC tag, a maltose binding protein and others known in the art. The presently disclosed subject matter also provides nucleic acids encoding such fusion proteins, vectors containing fusion protein-encoding nucleic acids and host cells comprising such nucleic acids or vectors. In certain embodiments, fusions can be made at the amino terminus (N-terminus) of a GPRC6A receptor or at the carboxy terminus (C-terminus) of a GPRC6A receptor.

In certain embodiments, the GPRC6A receptors disclosed herein can contain additional amino acids at the N-terminus and/or at the C-terminus end of the sequences, e.g., when used in the methods of the disclosed subject matter. In certain embodiments, the additional amino acids can assist with immobilizing the polypeptide for screening purposes, or allow the polypeptide to be part of a fusion protein, as disclosed above, for ease of detection of biological activity.

3. Methods for Identifying GPRC6A Receptor Modulating Compounds

The present disclosure further provides methods for identifying compounds that modulate the activity and/or expression of a GPRC6A receptor. For example, and not by way of limitation, the modulator can be an agonist (for example, a full or partial agonist), or an antagonist, or an inverse agonist, or an allosteric modulator. The presently disclosed subject matter provides in silico and in vitro methods for identifying compounds that modulate the activity and/or expression of a GPRC6A receptor, disclosed above.

3.1 in Silico Methods

The presently disclosed subject matter further provides in silico methods for identifying compounds that can potentially interact with a GPRC6A receptor and/or modulate the activity and/or expression of a GPRC6A receptor.

In certain embodiments, the method can include predicting the three-dimensional structure (3D) of a GPRC6A receptor and screening the predicted 3D structure with putative GPRC6A receptor modulating compounds (i.e., test compounds). The method can further include predicting whether the putative compound would interact with the binding site of the receptor by analyzing the potential interactions with the putative compound and the amino acids of the receptor. The method can further include identifying a test compound that can bind to and/or modulate the biological activity of the GPRC6A receptor by determining whether the 3D structure of the compound fits within the binding site of the 3D structure of the receptor.

In certain embodiments, the GPRC6A receptor for use in the disclosed method can be a feline GPRC6A, a canine GPRC6A, a human GPRC6A or any functional fragment thereof.

In other embodiments, the GPRC6A receptor for use in the disclosed method can comprises a polypeptide having any one of the amino acid sequence set forth in SEQ ID NOs: 4-6, or a fragment or variant thereof. In certain embodiments, the GPRC6A receptor for use in the presently disclosed subject matter can include a receptor comprising an amino acid sequence having at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% identity to any one of the amino acid sequence set forth in SEQ ID NOs: 4-6, or a fragment or variant thereof. In certain embodiments, the GPRC6A receptor for use in the disclosed method can be encoded by a nucleic acid having any one of the nucleotide sequence set forth in SEQ ID NOs: 1-3, or a fragment or variant thereof. In certain embodiments, the GPRC6A receptor for use in the presently disclosed subject matter can include a receptor encoded by a nucleotide sequence having at least 85%, at least 90%, at least 91%, at least 92%, at least 93%, at least 94%, at least 95%, at least 96%, at least 97%, at least 98% or at least 99% identity to any one of the nucleotide sequence set forth in SEQ ID NOs: 1-3, or a fragment or variant thereof.

Non-limiting examples of compounds (e.g., potential GPRC6A receptor modulators) that can be tested using the disclosed methods include any small chemical compound, or any biological entity, such as peptides, salts, amino acids and compound known in the art. In certain embodiments, the test compound can be a small chemical molecule.

In certain embodiments, structural models of a GPRC6A receptor can be built using crystal structures of other GPCRs as templates for homology modeling. For example, and not by way of limitation, structural models of the Venus flytrap domain can be generated using the crystal structures of Class C GPCRs. In certain embodiments, a structural model of a GPRC6A receptor can be based on a known or a combination of known crystal structures of GPCRs. (See, e.g., Lee et al., Eur J Pharmacol. 2015 May 14. pii: S0014-2999(15) 30012-1, which is incorporated by reference in its entirety herein). In certain embodiments, a structural model of the GPRC6A Venus flytrap domain can be generated using the crystal structure of the human calcium-sensing receptor 5K5S. In certain embodiments, the seven-transmembrane domain (7TM) of a GPRC6A receptor can be generated based on existing crystal structures of the 7TM domains of GPCR's. In certain embodiments the 7TM domain of a GPRC6A receptor can be generated based on existing crystal structures of the 7TM domain of class C GPCR's. In certain embodiments the 7TM domain of a GPRC6A receptor can be generated based on existing crystal structure 4OR2 of the 7TM domain of the Class C GPCR mGluR1. In certain embodiments the 7TM domain of a GPRC6A receptor can be generated based on the existing crystal structure 4O09 of the 7TM domain of the Class C GPCR mGluR5. In certain embodiments the 7TM domain of a GPRC6A receptor can be generated based on both 4OR2 and 4O09.

Any suitable modeling software known in the art can be used. In certain embodiments, the Modeller software package can be used to generate the three-dimensional protein structure.

In certain embodiments, the in silico methods of identifying a compound that binds to a polypeptide comprising a GPRC6A or a functional fragment thereof comprises determining whether a test compound interacts with one or more amino acids of a specific binding pocket, as described herein.

Compounds that are identified by the disclosed in silico methods can be further tested using the in vitro and in vivo methods disclosed herein.

3.2 Flytrap and Transmembrane Binding Sites

The present application provides for in silico methods of screening for compounds that modulate the activity of a GPRC6A receptor, wherein the compounds interact with one or more amino acids of the GPRC6A receptor. In certain embodiments, the GPRC6A receptor is a feline GPRC6A receptor. In certain embodiments, the feline GPRC6A receptor has the amino acid sequence set forth in SEQ ID NO: 4. In certain embodiments, the GPRC6A receptor is a canine GPRC6A receptor. In certain embodiments, the canine GPRC6A receptor has the amino acid sequence set forth in SEQ ID NO: 5. In certain embodiments, the GPRC6A receptor is a human GPRC6A receptor. In certain embodiments, the human GPRC6A receptor has the amino acid sequence set forth in SEQ ID NO: 6. In certain embodiments, the binding site of a GPRC6A receptor comprises amino acids within the Venus flytrap domain of the receptor, and can be identified by generating an interaction map of the receptor with active ligands using in silico modeling, as described herein. In certain embodiments the binding site of a GPRC6A receptor comprises amino acids within the 7TM domain of the receptor, and can be identified by generating an interaction map of the receptor with active ligands using in silico modeling as described herein. In one non-limiting example, the presence of an amino acid in the 7TM interaction map or the VFT interaction map means that the residue is in the vicinity of the ligand binding environment and interacts with the ligand.

In certain embodiments, the interaction between an amino acid in the 7TM interaction map or the VFT interaction map and the ligand is a pi-pi interaction.

In certain embodiments, the interaction between an amino acid in the 7TM interaction map or the VFT interaction map and the ligand is a hydrogen bond interaction.

In certain embodiments, the interaction between an amino acid in the 7TM interaction map or the VFT interaction map and the ligand is a hydrophobic interaction.

In certain embodiments, the interaction between an amino acid in the 7TM interaction map or the VFT interaction map and the ligand is a van de Waals interaction.

In certain embodiments, the amino acid in the 7TM interaction map or the VFT interaction map is a polar amino acid, wherein the amino acid interacts with the ligand as a hydrogen bond donor and/or acceptor.

In certain embodiments, the interaction between a compound and one or more amino acids of the GPRC6A receptors described herein can comprises one or more hydrogen bond, covalent bond, non-covalent bond, salt bridge, physical interaction, and combinations thereof. The interactions can also be any interaction characteristic of a ligand receptor interaction known in the art. Such interactions can be determined by, for example, site directed mutagenesis, x-ray crystallography, x-ray or other spectroscopic methods, Nuclear Magnetic Resonance (NMR), cross-linking assessment, mass spectroscopy or electrophoresis, cryo-microscopy, displacement assays based on known agonists, structural determination and combinations thereof. In certain embodiments, the interactions are determined in silico, for example, by theoretical means such as docking a compound into a specific binding pocket using molecular docking, molecular modeling, molecular simulation, or other means known to persons of ordinary skill in the art. In certain embodiments, the GPRC6A receptor is a feline GPRC6A.

In certain embodiments, the compounds interact with a GPRC6A receptor described herein according to any combination of interactions described herein, for example, one, two, three or more of the interactions.

In certain embodiments, the compounds bind to at least one of the receptors described herein. In certain embodiment, the compounds bind selectively to only one of the receptors described herein.

In certain embodiments, the GPRC6A receptor is a feline GPRC6A receptor having the amino acid sequence set forth in SEQ ID NO: 4. In certain embodiments, the amino acid residues that the compounds interact with comprises amino acid residues in the Venus flytrap domain (VFT), for example, Ser149, Glu170, Thr172, Tyr220, Arg279, Asp303, Asn304, Asn400 and any combination thereof. In certain embodiments, the amino acid residues that the compounds interact with comprises amino acid residues in the seven-transmembrane domain (7TM), for example, Arg662, Gln663, Phe666, Gly667, Phe670, Gln715, Glu746, Ala751, Phe752, Met755, Leu756, Ile759, Tyr793, Trp797, Phe800, Tyr804, Glu816, Val819, Ile820, and any combination thereof.

3.3 In Vitro Methods

The presently disclosed subject matter further provides in vitro methods for identifying raw materials for generating pet food, food products, or compounds that can modulate the activity and/or expression of a GPRC6A receptor, e.g., a feline GPRC6A receptor, a canine GPRC6A receptor or a human GPRC6A receptor.

GPRC6A receptors for use in the presently disclosed methods can include isolated or recombinant GPRC6A receptors or cells expressing a GPRC6A receptor, disclosed herein. In certain embodiments, the GPRC6A receptor for use in the disclosed methods can comprise any one of the amino acid sequences set forth in SEQ ID NOs: 4-6, or a fragment or variant thereof. In certain embodiments, the GPRC6A receptor for use in the disclosed method can have at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% identity to any one of the amino acid sequences set forth in SEQ ID NOs: 4-6, or a fragment or variant thereof. In certain embodiments, the GPRC6A receptor for use in the disclosed method can be encoded by a nucleotide sequence comprising SEQ ID NO: 1, or a fragment or variant thereof. In certain embodiments, the GPRC6A receptor for use in the presently disclosed subject matter can include a receptor encoded by a nucleotide sequence having at least 85%, at least 90%, at least 91%, at least 92%, at least 93%, at least 94%, at least 95%, at least 96%, at least 97%, at least 98% or at least 99% identity to any one of the nucleotide sequences set forth in SEQ ID NOs: 1-3, or a fragment or variant thereof.

In certain embodiments, the method for identifying compounds that modulate the activity and/or expression of a GPRC6A receptor comprises measuring the biological activity of a GPRC6A receptor in the absence and/or presence of a test compound. In certain embodiments, the method can include measuring the biological activity of a GPRC6A receptor in the presence of varying concentrations of the test compound. The method can further include identifying the test compounds that result in a modulation of the activity and/or expression of the GPRC6A receptor compared to the activity and/or expression of the GPRC6A receptor in the absence of the test compound.

In certain embodiments, the method can further include analyzing two or more, three or more or four or more test compounds in combination. In certain embodiments, the two or more, three or more or four or more test compounds can be from different classes of compounds, e.g., amino acids and small chemical compounds. For example, and not by way of limitation, the method can include analyzing the effect of one or more small chemical test compounds on the biological activity and/or expression of a GPRC6A receptor in the presence of one or more amino acid test compounds. In certain embodiments, the method for identifying the effect of a compound on the activity and/or expression of a GPRC6A receptor comprises analyzing the effect of a test compound on the biological activity and/or expression of a GPRC6A receptor in the presence of a GPRC6A receptor ligand, for example, a GPRC6A receptor agonist. In certain embodiments, the ligand is an L-amino acid. In certain embodiments, the L-amino acid is L-arginine, L-ornithine, L-lysine or any combination thereof.

In certain embodiments, the method for identifying the effect of a compound on the activity and/or expression of a GPRC6A receptor comprises analyzing the effect of a test compound on the biological activity and/or expression of a GPRC6A receptor in the presence of an allosteric modulator, for example, a positive allosteric modulator. In certain embodiments, the allosteric modulator is an alkaline earth cation (e.g., $Be^{2+}$, $Mg^{2+}$, $Ca^{2+}$, $Sr^{2+}$, and $Ba^{2+}$). In certain embodiments, the allosteric modulator is $Mg^{2+}$.

In certain embodiments, the method for identifying compounds that can modulate the activity and/or expression of a GPRC6A receptor comprises expressing a GPRC6A receptor in a cell line and measuring the biological activity of the receptor in the presence and/or absence of a test compound. The method can further comprise identifying test compounds that modulate the activity of the receptor by determining if there is a difference in receptor activation in the presence of a test compound compared to the activity of the receptor in the absence of the test compound. In certain embodiments, the method can include measuring the biological activity of the GPRC6A receptor in the presence of varying concentrations of the test compound. In certain embodiments, the selectivity of the putative GPRC6A receptor modulator can be evaluated by comparing its effects on other GPCRs or taste receptors, e.g., umami, fatty acid, kokumi (CaSR), TIR, etc. receptors.

In certain embodiments, the compounds identified according to the methods described herein increase or decrease the biological activity of a GPRC6A receptor by at least about 5%, 10%, 15%, 20%, 25%, 30%, 35%, 40%, 45%, 50%, 55%, 60%, 65%, 70%, 75%, 80%, 85%, 90%, 95%, 100%, or more, compared to the biological activity of the GPRC6A receptor when the compound is not present.

In certain embodiments, the method for identifying compounds that modulate the activity and/or expression of a GPRC6A receptor comprises determining whether a compound modulates the receptor directly, for example, as an agonist or antagonist. In certain embodiments, the method comprises determining whether a compound indirectly modulates the activity of the receptor (e.g., as an allosteric modulator), for example, by enhancing or decreasing the effect of other compounds on activating or inhibiting receptor activity.

In certain embodiments, the test agent that can modulate the activity and/or expression of a GPRC6A receptor has an EC50 value of no more than about 200 µM. In certain embodiments, the test agent has an EC50 value of no more than about 1 µM, 2 µM, 3 µM, 4 µM, 5 µM, 6 µM, 7 µM, 8 µM, 9 µM, 10 µM, 20 µM, 30 µM, 40 µM, 50 µM, 60 µM, 70 µM, 80 µM, 90 µM, 100 µM, 110 µM, 120 µM, 130 µM, 140 µM, 150 µM, 160 µM, 170 µM, 180 µM, 190 µM or 200 µM. In certain embodiments, the test agent has an EC50 value of no more than about 250 µM, 300 µM, 400 µM, 500 µM, 600 µM, 700 µM, 800 µM, 900 µM or 1 mM. In certain embodiments, the test agent has an EC50 value of at least 1 pM, 10 pM, 100 pM, 1 nM, 10 nM, or 100 nM, but no more than about 1 µM, 2 µM, 3 µM, 4 µM, 5 µM, 6 µM, 7 µM, 8 µM, 9 µM, 10 µM, 20 µM, 30 µM, 40 µM, 50 µM, 60 µM, 70 µM, 80 µM, 90 µM, 100 µM, 110 µM, 120 µM, 130 µM, 140 µM, 150 µM, 160 µM, 170 µM, 180 µM, 190 µM, 200 µM, 250 µM, 300 µM, 400 µM, 500 µM, 600 µM, 700 µM, 800 µM, 900 µM or 1 mM.

In certain embodiments, the test agent that can modulate the activity and/or expression of a GPRC6A receptor has an EC50 value of no more than about 50 mM. In certain embodiments, the test agent has an EC50 value of no more than about 1 mM, 2 mM, 3 mM, 4 mM, 5 mM, 6 mM, 7 mM, 8 mM, 9 mM, 10 mM, 20 mM, 30 mM, 40 mM or 50 mM. In certain embodiments, the test agent has an EC50 value of at least 1 nM, 10 nM, 100 nM, 1 µM, 10 µM, or 100 µM, but no more than about 1 mM, 2 mM, 3 mM, 4 mM, 5 mM, 6 mM, 7 mM, 8 mM, 9 mM, 10 mM, 20 mM, 30 mM, 40 mM or 50 mM.

In certain embodiments, the test agent that can modulate the activity and/or expression of a GPRC6A receptor has an Emax value of no less than about 2.0. In certain embodiments, the test agent has an Emax value of no less than about 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 40, 50, 60, 70, 80, 90, 100, 110, 120, 130, 140. 150 or 200. In certain embodiments, the test agent has an Emax value of more than about 200.

In certain embodiments, the modulation of the activity and/or expression of a GPRC6A receptor is measured using a relative activation of a test agent compared to a maximal stimulator, e.g., a percent activation compared to a maximal stimulator. In certain embodiments, the test agent has a percent activation compared to a maximal stimulator of no less than about 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 40, 50, 60, 70, 80, 90, 100, 110, 120, 130, 140. 150 or 200. In certain embodiments, the test agent has a percent activation compared to a maximal stimulator of more than about 200. In certain embodiments, the maximal stimulator comprises any GPRC6A agonists, e.g., Calindol, testosterone, L-amino acids, e.g., L-arginine, L-Lysine, L-ornithine, and any combination thereof. In certain embodiments, the maximal stimulator further comprises an allosteric modulator, e.g., a positive allosteric modulator. In certain embodiments, the allosteric modulator is an alkaline earth cation (e.g., $Be^{2+}$, $Mg^{2+}$, $Ca^{2+}$, $Sr^{2+}$, and $Ba^{2+}$). In certain embodiments, the allosteric modulator is $Mg^{2+}$. In certain embodiments, the maximal stimulator can be a nucleoside triphosphate. In certain embodiments, the nucleoside triphosphate is an adenosine triphosphate (ATP), a guanosine triphosphate (GTP), a cytidine triphosphate (CTP) and/or a thymidine triphosphate (TTP).

Activation of the receptor in the presently disclosed methods can be detected using a labelling compound and/or agent. In certain embodiments, the activity of the GPRC6A receptor can be determined by the detection of secondary messengers such as, but not limited to, cAMP, cGMP, IP3, DAG or calcium. In certain embodiments, the activity of the GPRC6A receptor can be determined by the detection of the intracellular calcium levels. Monitoring can be by way of, but not limited to, luminescence or fluorescence detection, such as by a calcium sensitive fluorescent dye or luminescent photoprotein. In certain embodiments, monitoring can be by way of luminescence. In certain embodiments, the intracellular calcium levels can be determined using a cellular dye, e.g., a fluorescent calcium indicator such as Calcium 4. In certain embodiments, the intracellular calcium levels can be determined by measuring the level of calcium binding to a calcium-binding protein, for example, calmodulin. Alternatively and/or additionally, the activity of the GPRC6A receptor can be determined by the detection of the phosphorylation, transcript levels and/or protein levels of one or more downstream protein targets of the GPRC6A receptor.

The cell line used in the presently disclosed methods can include any cell type that is capable of expressing a GPRC6A receptor (e.g., stable or transient expression). Non-limiting examples of cells that can be used in the disclosed methods include HeLa cells, Chinese hamster ovary cells (CHO cells), African green monkey kidney cells (COS cells), *Xenopus* oocytes, HEK-293 cells and murine 3T3 fibroblasts. In certain embodiments, the method can include expressing a GPRC6A receptor in HEK-293 cells. In certain embodiments, the method can include expressing a GPRC6A receptor in COS cells. In certain embodiments, the cells constitutively express the GPRC6A receptor. In certain embodiments, the cells transiently express the GPRC6A receptor. In another embodiment, expression of the GPRC6A receptor by the cells is inducible.

In certain embodiments, the cell expresses a calcium-binding photoprotein, wherein the photoprotein luminesces upon binding calcium. In certain embodiments, the calcium binding photoprotein comprises the protein clytin. In certain embodiments the clytin is a recombinant clytin. In certain embodiments, the clytin comprises an isolated clytin, for example, a clytin isolated from *Clytia gregarium*. In certain embodiments, the calcium-binding photoprotein comprises the protein aequorin, for example, a recombinant aequorin or an isolated aequorin, such as an aequorin isolated from *Aequorea victoria*. In certain embodiments, the calcium-binding photoprotein comprises the protein obelin, for example, a recombinant obelin or an isolated obelin, such as an obelin isolated from *Obelia longissima*.

In certain embodiments, expression of a GPRC6A receptor in a cell can be performed by introducing a nucleic acid encoding a GPRC6A receptor into the cell. For example, and not by way of limitation, a nucleic acid having the nucleotide sequence set forth in any one of SEQ ID NOs: 1-3, or a fragment thereof, can be introduced into a cell. In certain embodiments, the introduction of a nucleic acid into a cell can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cotton et al., Meth. Enzymol. 217:618-644 (1993); Cline, Pharmac. Ther. 29:69-92 (1985), the disclosures of which are hereby incorporated by reference in their entireties) and can be used in accordance with the disclosed subject matter. In certain embodiments, the technique can provide for the stable transfer of the nucleic acid to the cell, so that the nucleic acid is expressible by the cell and inheritable and expressible by its progeny. In certain embodiments, the technique can provide for a transient transfer of the nucleic acid to the cell, so that the nucleic acid is expressible by the cell, wherein the concentration of the nucleic acid and the expression decrease in subsequent generations of the cell's progeny.

In certain embodiments, the methods can include identifying compounds that bind to a GPRC6A receptor. The methods can comprise contacting a GPRC6A receptor with a test compound and measuring binding between the compound and the GPRC6A receptor. For example, and not by way of limitation, the methods can include providing an isolated or purified GPRC6A receptor in a cell-free system, and contacting the receptor with a test compound in the cell-free system to determine if the test compound binds to the GPRC6A receptor. In certain embodiments, the method can comprise contacting a GPRC6A receptor expressed on the surface of a cell with a candidate compound and detecting binding of the candidate compound to the GPRC6A receptor. The binding can be measured directly, e.g., by using a labeled test compound, or can be measured indirectly. In certain embodiments, the detection comprises detecting a physiological event in the cell caused by the binding of the compound to the GPRC6A receptor, e.g., an increase in the intracellular calcium levels. For example, and not by way of limitation, detection can be performed by way of fluorescence detection, such as a calcium sensitive fluorescent dye, by detection of luminescence, or any other method of detection known in the art.

In other non-limiting embodiments, the in vitro assay comprises cells expressing a GPRC6A receptor that is native to the cells. Examples of such cells expressing a native GPRC6A receptor include, for example but not limited to, dog and/or cat taste cells (e.g., primary taste receptor cells). In certain embodiments, the dog and/or cat taste cells expressing a GPRC6A receptor are isolated from a dog and/or cat and cultured in vitro. In certain embodiments, the taste receptor cells can be immortalized, for example, such that the cells isolated from a dog and/or cat can be propagated in culture.

In certain embodiments, expression of a GPRC6A receptor in a cell can be induced through gene editing, for example, through use of the CRISPR gene editing system to incorporate a GPRC6A receptor gene into the genome of a cell, or to edit or modify a GPRC6A receptor gene native to the cell.

In certain embodiments, the in vitro methods of identifying a compound that binds to a GPRC6A comprises determining whether a test compound interacts with one or more amino acids of a specific binding pocket, as described herein.

In certain embodiments, compounds identified as modulators of a GPRC6A receptor can be further tested in other analytical methods including, but not limited to, in vivo assays, to confirm or quantitate their modulating activity.

In certain embodiments, the methods of identifying a GPRC6A receptor modulator can comprise comparing the effect of a test compound to a GPRC6A receptor agonist or antagonist.

For example, a test compound that increases or decreases the activity of the receptor in the presence of an agonist when compared to the activity of the receptor when contacted with a GPRC6A receptor agonist alone can be selected as a GPRC6A receptor modulating compound.

GPRC6A receptor agonists that can be used according to said methods can comprise one or more compounds, including, but not limited to L-amino acids, e.g., L-arginine, L-Lysine and L-ornithine.

In certain embodiments, the GPRC6A receptor modulators of the present disclosure comprise a salt of the GPRC6A receptor modulator, for example, but not limited to, an acetate salt or a formate salt. In certain embodiments, the GPRC6A receptor modulator salt comprises an anion (−) (for example, but not limited to, $Cl^-$, $O^{2-}$, $CO_3^{2-}$, $HCO_3^-$, $OH^-$, $NO_3^-$, $PO_4^{3-}$, $SO_4^{2-}$, $CH_3COO^-$, $HCOO^-$ and $C_2O_4^{2-}$) bonded via an ionic bond with a cation (+) (for example, but not limited to, $Al^{3+}$, $Ca^{2+}$, $Na^+$, $K^+$, $Cu^{2+}$, $H^+$, $Fe^3$, $Mg^{2+}$, $NH_4^+$ and $H_3O^+$). In other embodiments, the GPRC6A receptor agonist salt comprises a cation (+) bonded via an ionic bond with an anion (−).

In certain embodiments, the GPRC6A receptor modulators of the present application are identified through in silico modeling of a GPRC6A receptor, e.g., a feline GPRC6A receptor, wherein the GPRC6A receptor modulators of the present application comprise a structure that fits within a binding site of the GPRC6A receptor. In certain embodiments, the in silico method comprises the in silico methods described above and in the Examples section of the present application.

In certain embodiments, the GPRC6A receptor modulators of the present application are identified through an in vitro method, wherein the GPRC6A receptor modulator compounds modulate a GPRC6A receptor, disclosed herein, expressed by cells in vitro. In certain embodiments, the in vitro method comprises the in vitro methods described above and in the Examples section of the present application.

4. Pet Food Products

The present application provides for screening methods that can be used to identify suitable raw materials to produce a palatable and nutritious pet food product. The presently disclosed screening methods can also be used to determine if a finished pet food product would be palatable to the pet (e.g., a cat). For example, the in vitro methods described herein can be used to screen raw materials and finished pet food products to identify whether the raw materials or finished pet food products comprise compounds that modulate GPRC6A receptor activity and/or expression. In certain embodiments, raw materials and finished pet food products that do not increase the activity and/or expression of a GPRC6A receptor can be selected for use in, or as, a pet food product for consumption. Non-limiting examples of suitable pet food products include wet food products, dry food products, moist food products, pet food supplements (e.g., vitamins), pet beverage products, snack and treats and pet food categories described herein.

One of the goals of the pet care industry is to identify sustainable protein sources for pets that do not compete with the human food chain. As such, there is an ongoing search for novel protein sources that fit these criteria. The presently disclosed screening method can be used to identify which of the novel protein sources would be considered palatable to the pet, or at least have no effect on the palatability of the other ingredients of the pet food. In certain embodiments, the novel protein source (i.e., raw material) is meat, fish, cheese, beans, yeast, yeast extracts, bacteria, algae, fungi, nuts, seeds or other plant material, or combinations thereof. In certain embodiments, the raw material is meat.

In certain embodiments, the protein source can be derived from a variety of plant sources. Non-limiting examples of plant sources include corn, maize, rice, soy, wheat, etc. For example, and not by way of limitation, the plant-derived protein can include lupin protein, wheat protein, soy protein and combinations thereof. Alternatively or additionally, the protein source can be derived from a variety of animal sources, for example, a multicellular eukaryotic organism from the kingdom animalia. Non-limiting examples of animal protein include beef, pork, poultry, lamb or fish including, for example, muscle meat, meat byproduct, meat meal or fish meal. Other non-limiting examples of animal sources include insects, or other organism from the phylum arthropoda.

In certain embodiments, the protein source can be derived from yeast or any other single-cell eukaryotic organisms, mold, mushroom or fungi.

In certain embodiments, the protein source can be derived from bacteria, archaea, or any other archaebacteria, eubacteria, or prokaryotic organism.

In certain embodiments, the protein source can be derived from algae, kelp, seaweed, or any other single or multicellular photosynthetic organism or protist.

In certain embodiments, the presently disclosed subject matter includes accepting or rejecting a raw material for the production of pet food based on the raw material's ability to enhance, increase, decrease and/or modulate the activity and/or expression of a GPRC6A receptor. In certain embodiments, the raw material is rejected if the raw material results in the enhancement or increase in the activity and/or expression of at least one GPRC6A receptor. In certain embodiments, the raw material is rejected if the raw material results in the enhancement or increase in the activity and/or expression of at least two, at least three, at least four, at least five, at least six, at least seven, at least eight, at least nine, at least ten, at least eleven, at least twelve, at least thirteen, at least fourteen, at least fifteen, and/or at least sixteen GPRC6A receptors. In certain embodiments, the raw material is accepted if it does not modulate the activity of at least one GPRC6A receptor. In certain embodiments, the raw material is selected if it inhibits or blocks the activity and/or expression of at least one GPRC6A receptor. In certain embodiments, the GPRC6A receptor is fGPRC6A.

In certain non-limiting embodiments, a raw material that results in the enhancement or increase in the activity and/or expression of at least one GPRC6A receptor can be admixed with a compound that inhibits or reduces the activity and/or expression of the at least one GPRC6A receptor, wherein the admixture is accepted for the production of pet food.

During the production of pet food, some of the materials may change form due to mechanical forces, thermal forces, or chemical reactions. The presently disclosed screening method can be used to identify pet food products that form compounds that are unpalatable to an animal, for example, a cat, for example, a compound that enhances or increases the activity and/or expression of a GPRC6A receptor.

In certain embodiments, the presently disclosed subject matter includes accepting or rejecting a pet food product based on the product's ability to enhance, increase, decrease and/or modulate the activity and/or expression of a GPRC6A receptor. In certain embodiments, the pet food product is rejected if the product results in the enhancement or increase in the activity and/or expression of at least one GPRC6A receptor. In certain embodiments, the pet food product is rejected if the product results in the enhancement or increase in the activity and/or expression of at least two, at least three, at least four, at least five, at least six, at least seven, at least eight, at least nine, at least ten, at least eleven, at least twelve, at least thirteen, at least fourteen, at least fifteen, and/or at least sixteen GPRC6A receptors. In certain embodiments, the pet food product is accepted if it does not modulate the activity of at least one GPRC6A receptor. In certain embodiments, the pet food product is selected if it inhibits or blocks the activity and/or expression of at least one GPRC6A receptor. In certain embodiments, the GPRC6A receptor is fGPRC6A.

The flavor compositions of the present disclosed subject matter can also be used in a wide variety of pet food products. The combination of the flavoring composition(s) of the presently disclosed subject matter together with a pet food product and optional ingredients, when desired, provides a flavoring agent that possesses unexpected taste and imparts, for example, a desirable umami and/or kokumi sensory experience. The flavor compositions disclosed herein can be added prior to, during or after formulation processing or packaging of the pet food product, and the components of the flavor composition can be added sequentially or simultaneously.

In certain embodiments, the pet food product is a nutritionally complete dry, wet or semi-moist food product. A dry or low moisture-containing nutritionally-complete pet food product can comprise less than about 15% moisture. A wet or high moisture-containing nutritionally-complete pet food product can comprise greater than about 50% moisture. Such food products can include from about 10% to about 90% fat, from about 10% to about 70% protein and from about 5% to about 80% carbohydrates, e.g., dietary fiber and ash, on a percent energy basis.

In certain embodiments, the pet food product is a nutritionally complete dry, wet or semi-moist food product. In certain embodiments, the pet food product includes from about 60% fat, from about 30% protein and from about 10% carbohydrates, e.g., dietary fiber and ash, on a percent energy basis.

In certain embodiments, the pet food product is a nutritionally complete moist food product. A moist, e.g., semi-moist or semi-dry or soft dry or soft moist or intermediate or medium moisture containing nutritionally-complete pet food product comprises from about 15 to about 50% moisture.

In certain embodiments, the pet food product is a pet food snack product. Non-limiting examples of pet food snack products include snack bars, pet chews, crunchy treats, cereal bars, snacks, biscuits and sweet products.

In certain embodiments of the present disclosure, the taste and/or palatability attributes of a pet food product or medicine prepared according to the methods described herein can be measured by an in vivo tasting method that uses a panelist of taste testers. For example, but not by way of limitation, the panel can contain feline panelists. In certain embodiments, the palatability of a pet food product containing, for example, a screened raw material or a screened pet food product can be determined by the consumption of the pet food product alone (e.g., the one bowl test, monadic ranking). In certain embodiments, the palatability of a screened raw material or a screened pet food product can be determined by the preferential consumption of the pet food product or raw material, versus a pet food product that is known to be palatable to the animal (e.g., the two bowl test for testing preference, difference and/or choice).

In certain embodiments, the palatability of a compound identified according to the methods described herein can be determined by the preferential consumption of a water solution containing said compound versus a water solution that does not contain the compound or contains a different flavor composition, for example, a GPRC6A receptor agonist (e.g., the two bottle test). The intake ratio for each pet food product or water solution can be determined by measuring the amount of one ration consumed divided by the total consumption. The consumption ratio (CR) can then be calculated to compare the consumption of one ration in terms of the other ration to determine the preferential consumption of one food product or water solution over the other. Alternatively or additionally, the difference in intake (g) can be used to assess the average difference in intake between the two solutions in a two bottle test or between two pet food products in a two bowl test at a selected significance level, for example, at the 5% significance level to determine an average difference in intake with a 95% confidence interval. In certain embodiments, the confidence interval can be about 90%. However, any significance level may be used, for example, a 1, 2, 3, 4, 5, 10, 15, 20, 25 or 50% significance level.

In certain embodiments, percentage preference scores, e.g., the percentage preference for one solution or food product by an animal, is the percentage of the total liquid or food product ingested during the test that that solution or food product accounts for, can also be calculated.

EXAMPLES

The presently disclosed subject matter will be better understood by reference to the following Examples, which are provided as exemplary of the invention, and not by way of limitation.

Example 1—in Silico Model of Interactions Between Feline GPRC6A Receptors and Putative Binding Compounds The present example describes the computational modeling of feline GPRC6A receptor to identify putative GPRC6A receptor modulators. A structural homology model of the Venus flytrap domain of fGPR6A was generated based on a crystal structure of the active form of the extracellular domain of the Class C human calcium-sensing receptor (Protein Data Bank (PDB) Accession code 5K5S; see Geng Y. et al., Structural mechanism of ligand activation in human calcium-sensing receptor. Elife, 2016 July 19;5.). Resulting residues lining the Venus flytrap domain of the fGPR6A model that can interact with agonists or antagonists and can comprise in part the Venus flytrap domain active site include Ser149, Glu170, Thr172, Tyr220, Arg279, Asp303, Asn304, and Asn400.

Similarly, a structural homology model of the transmembrane fGPR6A domain was generated based on the crystal structures 4OR2 and 4009 from the PDB. 4OR2 is the crystal structure of the transmembrane domain of mGluR1 from Group C GPCR bound to a negative allosteric modulator (Wu et al., Science, 344(6179):58-64 (2014). 4009 is the crystal structure of the transmembrane domain of mGluR5, a Group C GPCR, bound to a negative allosteric modulator (see Dore et al., Nature 511:557-562 (2014). The resulting modeled transmembrane active site includes residues Arg662, Gln663, Phe666, Gly667, Phe670, Gln715, Glu746, Ala751, Phe752, Met755, Leu756, Ile759, Tyr793, Trp797, Phe800, Tyr804, Glu816, Val819, and Ile820 (see helix assignments in figure description).

Homology models were built using the homology modeling program Modeler and the energy-based simulation program Charmm from the Discovery Studio (DS) suite of programs from Biovia (Eswar et al., Current Protocols in Bioinformatics, Supplement 15:5.6.1-5.6.30 (2006)). Ligands were docked into the active site using the docking program BioDock from BioPredict and refined using energy minimization and molecular dynamics in Charmm. In addition, any suitable modeling, docking, and minimization and simulation software known in the art could be used for the same purpose. Exemplary modeling results of GPRC6A modulators, e.g., L-lysine, L-arginine, testosterone and Calindol, are shown in FIGS. 5A-8B.

Example 2-Identification of Feline GPRC6A Receptor Modulators Using In Vitro Assays In vitro functional characterization of the selected modulators was used to evaluate the effectiveness of the putative modulator compounds in modulating the activation of a GPRC6A receptor.

Methods

All transient transfections were performed with Lipofectamine2000 (Life Technologies) according to the manufactures protocol.

The HEK-293 T-REX/natClytin cell line was stably transfected by electroporation. Briefly, $3\times10^6$ cells detached from 60% confluent flasks were transfected with 10 μg of DNA construct by using the Gene Pulser II electroporator (Biorad) (parameters: 300 Volts, 950 μF). When co-transfections were carried out (fGPRC6A+GaqG66D), a molar ratio of 1:1 was used. Transfected cells were diluted in wild-type complete medium and seeded in T75 flask. After 72 h, the proper antibiotic concentration was added to the medium and cells were cultured for about 2-3 weeks in order to generate stable pools.

Activation of the fGPRC6A receptor was determined by detecting a change in intracellular calcium levels as measured by fluorescence of the calcium sensitive fluorescent dye (e.g., Fluo-4 AM dye) or luminescence of the luminescent photoprotein (e.g., nat-Clytin). Cells that did not express the fGPRC6A receptor (MOCK control) were used as a control. A FLIPRR Tetra system was used to measure fluorescence or luminescence.

Results

HEK293 cells that transiently or stably expressed the fGPRC6A taste receptor, were exposed to compounds to determine whether the compounds modulated the activity of the fGPRC6A receptor. In particular, HEK-293 TREx/nat-Clytin cell line was used as recipient cell line and stable transfections were carried out using an inducible expression construct encoding for the feline GPRC6A in combination with the chimeric Ga protein GaqG66D. Stable pools underwent a first limiting dilution (LD) and the best clones were chosen after stimulation with the reference ligand L-Arg+20 mM $Mg^{2+}$, using both a fluorescent and a luminescent read-out. Four selected first LD clones were subjected to a second round of LD; CPA was then performed in order to choose the best performing clones. On the basis of the functional data obtained at FLIPR® Tetra, the final K2.3 clone was chosen for the subsequent optimization steps. Fluorescence (Fluo-4 AM dye) was chosen as best read-out given its higher sensitivity in comparison to luminescence.

In particular, cells were seeded at 7,500 cells/well and tested 48 h after seeding (Doxycycline was added at 1 μg/mL 24 h after seeding). Then, medium was removed, and cells were incubated with Fluo-4 AM dye (20 μL/well) for 1 h at 37° C. After the incubation and the washing steps, cells were injected with increasing concentrations (10 μL/well, 3X) of the following ligands, in the presence or absence of 20 mM Mg2+(DMSO 0.5% final concentration):

L-Arginine+20 mM Mg2+(complete D/R, starting from 1 mM, 1:3.162 dilution range)

L-Ornithine+20 mM Mg2+(complete D/R, starting from 1 mM, 1:3.162 dilution range)

L-Lysine+20 mM Mg2+(complete D/R, starting from 1 mM, 1:3.162 dilution range)

L-Arginine (complete D/R, starting from 1 mM, 1:3.162 dilution range)

L-Ornithine (complete D/R, starting from 1 mM, 1:3.162 dilution range)

L-Lysine (complete D/R, starting from 1 mM, 1:3.162 dilution range)

NPS R-568 (complete D/R, starting from 30 μM, 1:3.162 dilution range)

Figure 9A:
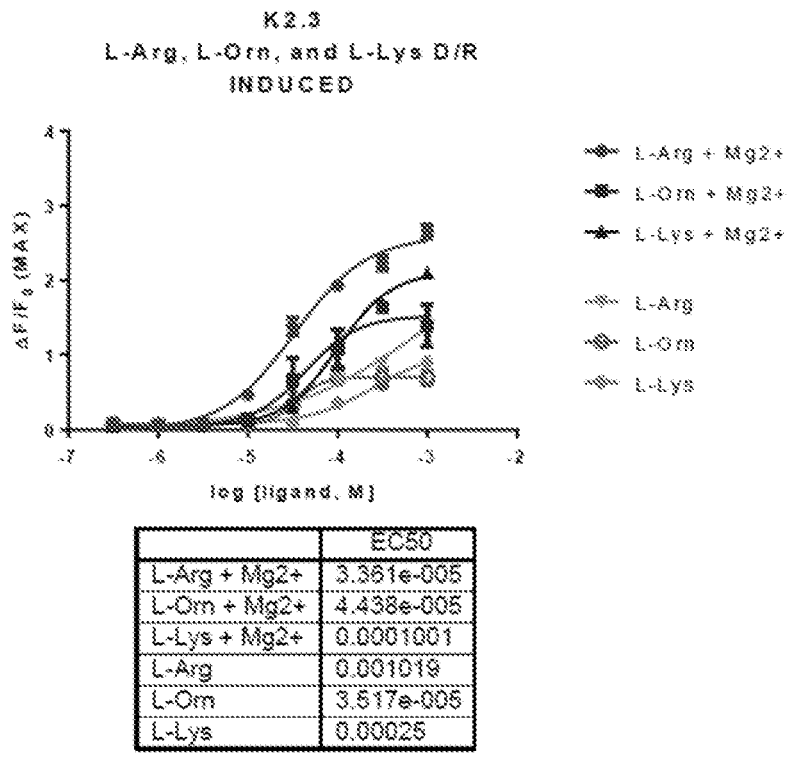
Figure 9B:
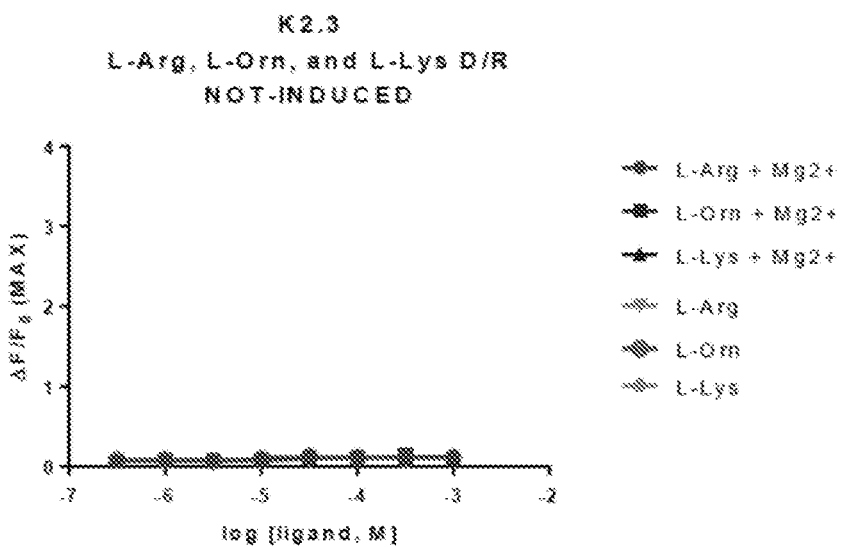

The sigmoidal dose-response curves are reported in FIGS. 9A-9C. The results indicated that a specific response to L-alpha-amino acids could be observed also in the absence of $Mg^{2+}$, although with higher EC50 values as well as lower fluorescent signals. $Mg^{2+}$ could therefore be considered a positive allosteric modulator of the tested L-alpha-amino acids. L-Arg (in combination with $Mg^{2+}$) was chosen as reference agonist, given its potency and the fluorescent signal triggered upon stimulation with this activator. The NPS R-568 compound, that is reported to stimulate GPRC6A-mediated EKR activity (Pi M et al., 2005), was not functional in the present cell-based assay. The receptor was not activated by magnesium ion alone.

Example 3—Feeding Test to Determine Feline Response to GPRC6A Modulators

The present example describes a feeding test to feline response to GPRC6A modulators.

Figure 10:
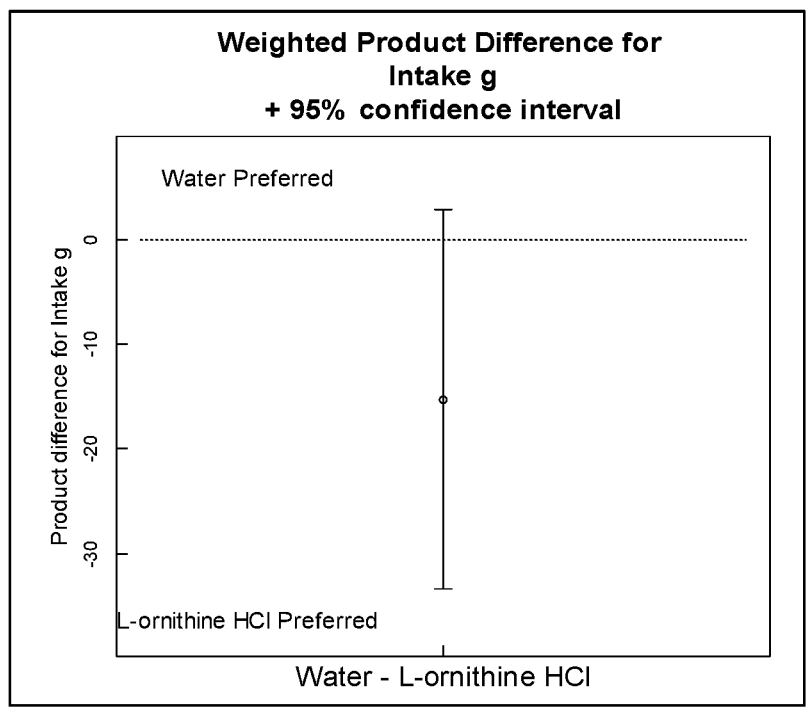
FIG. 10 depicts cat feeding test results. The intake of water containing L-ornithine was on average 15.28 g more that the intake of plain water.

Cats were allowed access to water containing 0.15 mM L-ornithine hydrochloride and to plain water. The methodology used a 2-bottle choice test with 24 cats (the final number of cats for each test can vary due to data being discarded by spillage, etc.). Cats were housed individually during trial periods and had free access to water available between testing periods. The test involved a choice test between the tastant/mixture at a given concentration dissolved in deionized water versus deionized water only or another tastant/mixture. Control was made for positional bias (e.g., A/B exposure 1 and B/A exposure 2) and evaporation loss. The testing time was 36 hours (i.e., 18 hours per day, allowing a two-day crossover). Following two consecutive days of each testing, cats had two consecutive days of rest. Cats were offered a dry diet as a single meal at the start of the test period for one hour, calculated to meet the individual requirements for each cat. As shown in FIG. 10, the intake of water containing L-ornithine was on average 15.28 g more that the intake of plain water.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

What is claimed is:

1. A method for identifying a compound that modulates the activity of a feline GPRC6A receptor comprising the amino acid sequence set forth in SEQ ID NO: 4, the method comprising
   (a) detecting an in silico interaction between a test agent and one or more amino acid residues in the seven transmembrane domain (7TM) of the receptor, wherein the one or more amino acid residues are selected from the group consisting of Arg662, Gln663, Phe666, Gly667, Phe670, Gln715, Glu746, Ala751, Phe752, Met755, Leu756, Ile759, Tyr793, Trp797, Phe800, Tyr804, Glu816, Val819, Ile820, and any combination thereof,
   (b) contacting the test agent with a cell comprising an exogenous feline GPRC6A receptor or a functional fragment thereof,
   (c) measuring a biological activity of the exogenous feline GPRC6A receptor, and
   (d) selecting as the compound, a test agent that increases or decreases the activity of the polypeptide.

2. The method of claim 1, wherein step (d) comprises selecting as the compound, a test agent that decreases the activity of the receptor.

3. The method of claim 1, wherein step (d) comprises selecting as the compound, a test agent that increases the activity of the receptor.

4. The method of claim 1, further comprising determining an EC50 value of the compound.

5. The method of claim 1, further comprising detecting an in silico interaction between the test agent and one or more amino acid residues in the Venus flytrap domain (VFT), wherein the one or more amino acid residues are selected from the group consisting of Ser149, Glu170, Thr172, Tyr220, Arg279, Asp303, Asn304, Asn400, and any combination thereof.

6. The method of claim 1, wherein the cell expresses a calcium-binding photoprotein.

7. The method of claim 1, wherein the biological activity of the receptor is measured by monitoring a calcium concentration or a cGMP activity within the cell.

8. The method of claim 7, wherein the calcium concentration is monitored by fluorescence detection or luminescence detection.

9. The method of claim 8, wherein the fluorescence detection comprises a calcium sensitive fluorescent dye.

* * * * *

SEQUENCE LISTING

```
<160> NUMBER OF SEQ ID NOS: 6

<210> SEQ ID NO 1
<211> LENGTH: 2787
<212> TYPE: DNA
<213> ORGANISM: Felis catus
<220> FEATURE:
<221> NAME/KEY: Cat GPRC6A
<222> LOCATION: (1)..(2781)
<223> OTHER INFORMATION: Cat GPRC6A nucelotide sequence

<400> SEQUENCE: 1
atggcactat tgattacact gattacctgt tttgtgattc ctcttgctac ttcccagact      60
tgccagaccc ctgacgactt cgtggctgcc acttctccag ggcatgtcat aattggaggt     120
ttattcgcca tcatgaaaaa aatgctgtcc tcagaagact atcccagacg accagaaatc     180
cagaagtgtg ttgggtttga aatatcaatt tttcttcaaa ctcttgccat gattcacagc     240
attgagatga tcaataattc aacactatta tctggaatca aactggggta tgaaatctat     300
gacacttgta cagaagtcac agtggcaatg gcagccgctc tgaggtttct ttctaagttc     360
aacagctcca gagaaatcat ggagtttaaa tgtgactatt ccagctacat gccaagggtt     420
aaggctgtca taggtgctgg ctactcagaa ataaccatgg ctgtctccag gatgttgaat     480
ttacagctta tgccacaggt gagttatgaa tcaactgcag aaatcctaag tgacaaaatt     540
cgctttcctt cattttttacg gactgtgccc agtgacttct atcaaactaa agcaatggcc     600
cacctgattg agaagtctgg atggaactgg attggcatca tagccacaga tgatgactat     660
ggacgaatgg ccctcaacac ttttgcagtt cagaccacag caaataatgt gtgcatagct     720
ttcaaagaag ttctcccagc cttcctctca gataatacca tcgaagtcag gatcaatgag     780
acacttgaga aaatcatagc agaagcccag gttaatgtca ttgtggtatt cctgaggcaa     840
ttccatgttt tcaatctctt cagtaaagct ctagaaagga atataaataa gatatggatt     900
gctagtgata actggtcaac ggccaccaag attacaacca ttcctaatgt taaaaggatt     960
ggcaaagttg tagggtttac ctttagaaga gggaatatgt cttccttcca ttcctttctt    1020
caaaatctgc atatatttcc cagtgataat aacaaggtct aaatgaata tgccacactc    1080 ttgtctgctt gtgcatatgt caaggacagt gatttgagtc agtgcatttc caaccattct    1140
caggggactt tggcctacaa ggttaacaag gatatagaaa ggaacttctc cctgagaaat    1200
gatttcctgt ggaattatac tgagccaggc cttgttcaca gtatccagct tgcagtactt    1260
gctcttggtt atgccattcg ggatctctgc caagctcgcg actgtcagaa ccccaacgcc    1320
tttcaaccat gggagttact tgatgcacta aaaaatgtga cattcactga tgaagggaat    1380
tcatttcatt ttgatgctca tgggatatg aatactggat atgatgttgt gctctggaag    1440
gagattgatg gtcacctgac tatcaccaag atagcacaat atgatctgaa gaatgatgtc    1500
ttcgtcatca cagaccaaga aacaaaaaat gagttcagaa atcttaagca aattcagtct    1560
aaatgctcca aggagtgcag tcctgggcaa atgaagaaaa ctacaagaag tcaacatatc    1620
tgctgctatg aatgtgtgaa ctgtcctgaa aatcactaca gtaaccagac agatatggat    1680
cactgccttt tatgtaacaa cgaaactcag tgggcccctg taaagagcac agcatgcttt    1740
gaaaaggaag tggagtatct cagttggaat gactccttgg ccatactgct cctggccctc    1800
```

```
tccctactag gaatcatgtt tgttctggcc attggcataa tatttacaag aaacctgaac    1860
acgcctgttg tgaaatcgtc cgggggattg ctggtctgct atgtgatcct tctctgtcat    1920
ttcctcaact ttgccagcac gggcttttc attggagaac cacaagactt cacatgtaaa    1980
accaggcaga cgttttttgg tgtgagcttc actctctgca tctcctgcat tttggtgaag    2040
tccctgaaaa ttctgctagc cttcagcttc gaccccaagt tgcagaactt cctgaagtgc    2100
ctctataaac ccatccccat catcttcatt tgcacaggta tccaggttgc catttgcaca    2160
gtctggctaa tctttgcagc acctgctgtg aagagaatg tctccttgcc cagagtcatt    2220
atcctggaat gtgaggaggg atccatcctt gcatttggca tcatgctggg ctatattgcc    2280
atcctggcct tcatttgctt catatttgcc ttcaaaggca ggaaactacc cgagaattac    2340
aatgaagcca aattcataac atttggcatg ctcgtttatt tcatagcttg gatcacattc    2400
gtccccgtct atgctaccac atttggtaaa tatttaccag ctgtggagat tatcattatt    2460
ttaatatcga actatgggat cctgtgttgc acattcttcc ccaaatgcta tgttattctt    2520
tataagcagg agactaacac aaaatctgcc tttctcaaga tgatttacag ttactcttcc    2580
cacagcgcaa gcagccttgc catgagtcac gtttccctgg actcctctag cagcaacatc    2640
acagcgacca atcccagctc cggtggcagg cctgcagcct ggcaggaaag cagggatatc    2700
cgggcacaag catttgcaca cacacgcaga gaaaacgctg caagtatgtc taaaacttgg    2760
cctcggaaaa gaatttcaag tatttga                                        2787

<210> SEQ ID NO 2
<211> LENGTH: 2787
<212> TYPE: DNA
<213> ORGANISM: Canis familiaris
<220> FEATURE:
<221> NAME/KEY: Dog GPRC6A
<222> LOCATION: (1)..(2787)
<220> FEATURE:
<221> NAME/KEY: Dog GPRC6A
<222> LOCATION: (1)..(2787)
<223> OTHER INFORMATION: Dog GPRC6A nucleotide sequence

<400> SEQUENCE: 2
atggcactat tgattatacc gattacctgc tttgggagta ctcttgttac ttcccagcct      60
tgccagactc ctgatgactt tgtggctgcc acttctccag acatatcat gattggaggt     120 ttatttgcca ttcatgagaa aatgctgccc tcagaagact atcccagacg accagaaatc     180
cagaagtgtg ttggctttga aatatcaatt tttcttcaaa ctcttgccat gattcatagc     240
attgagatga tcaacaattc aacactatta tccggagtca aactggggta tgaaatctat     300
gacacctgta ccgaagtcac agtggcgatg cagccactc tgaggtttct ctctaagcgc     360
aactgctcca gagaaattgt ggagtttaag tgtgattatt ccagctacat gccaagagtt     420
aaggctgtaa taggtgctgg ctactcagaa ataacaatgg ctgtctccag gatgctgaat     480
ttacagctca tgccacaggt gagttatgaa tcaactgcag aaatcctaag tgacaaaatt     540
cgctttcctt cattttacg gactgtgccc agtgacttct atcaaactaa agcaatggcc     600
cacctgattc agaaatctgg atggaactgg attggcatca tagccacaga tgatgactac     660
ggacgactgg ccctcaacac ttttgcagtt cagaccgcag caaataatgt gtgcatagct     720
ttcaaggagg ttctcccagc cttcctctca tgatgatacca ttgaaatcag gatcaatgag     780
acccttgaga aaatcatcgc agaagcccag gttaatgtca ttgtggtatt tctgaggcaa    840
ttccatgttt tcaatctctt cactaaagct atagaaaaga atataataa gatctggatt      900
```

```
gccagtgata actggtccat ggccaccaag atcaccacca tccctaatgt taaaaggatt      960
ggcaaagttg tggggtttac ctttagaaga gggaatatgt cttctttcca ctcctttctt     1020
caaaacttgc atatgtttcc cagagataat aacaagcccc taaatgaata tgccatgctc     1080
ttgtctgcct gtgcacatgt caaggacagt gatttgagtc agtgcatttc agccgctct      1140 cgggggactt tggcctacac ggctaacaag gatatagaaa ggaacttctc cctgagaaat     1200
gatttcctgt gggattacac cgagccggga cctgttcaca gtatccagct cgcagttctt     1260
gcccttggtt atgccattcg ggatctctgc caagctcgag actgtcagaa ccccaacgcc     1320
tttcaaccat gggagttact tgatgtatta aaaaatgtga cattcactga tgaagggaat     1380
tcatttcatt ttgatgccca tggggatatg aatactggat atgatgttgt gctctggaag     1440
gagattggcg gccacatgac tatcaccaag atggcacaat atgatctgag gaatgatgtc     1500
ttcatcatca cagaccaaga aacaaaaaat gagttcagaa atcttaagca aattcgatct     1560
aaatgctcca aggaatgcag tcctgggcaa atgaaaaaaa ctacaagaag tcaacatatc     1620
tgctgctatg aatgtgtgga ctgtcctgaa atcactaca gtaaccagac agatatggat     1680
cactgcctct tatgcaacaa tgaaactcac tgggcccctg tcaggagcac aaggtgcttt     1740
gaaaaggaag tggaatatct caactggaat gattccttgg ctatactgct cctggccctc     1800
tccctactag gaatcatcct tgttctggcc attggcataa tatttacaag aaacctgaac     1860
acacccattg taaaatcatc tggggattg ctggtctgct acgtgatcct tctctgtcat     1920
gtcctcaact tcgccagcac aggcttcttc attggagaac cacaagactt cacatgtaaa     1980
accaggcaga ctgtatttgg tgtgagcttc actctctgca tctcctgcat tttgatgaag     2040
tccctgaaaa ttctgctagc cttcagcttc gatcccaagt tgcagaactt cttgaagtgc     2100
ctctataaac cgatccccat catcttcact tgcacaggta tccaggttgt catttgcaca     2160
atctggctaa tctttgcagc acctgctgtg gaagagaatg tctccttgcc cagagtcatt     2220
atcctggaat gtgaggaggg atccgtcctt gcatttggca ccatgctggg ttatattgcc     2280
atcctggcct tcatttgctt catatttgca ttcaaaggca ggaaattacc tgagcattac     2340
aacgaagcca aattcataac atttggcatg ctcatttatt tcatagcttg gatcacattc     2400
atccccatct atgctaccac atttggtaaa tatttgccag ctgtggagat tattgttatt     2460
ttaatttcta actatgggat cctgtgttgc acattcttcc ccaaatgcta tattattctt     2520
tgtaagcaag aggctaacac aaaaatctgc ctttctcaaga tgatttacag ttactcttcc     2580
cacactgcaa gcagccttgc cattagtcat gtttcactgg actccactaa cagcagtatc     2640
acaacgacca atcccagctc tagtggcaag tctgcagcct ggcaggaaag caaggatctt     2700
caggcacaag catttgcaca catatgcaga gaaaatgcga taagtgtacc taaaatttta     2760
cctcgaaaaa gaatttcaag tatatga                                        2787
```

<210> SEQ ID NO 3
<211> LENGTH: 2781
<212> TYPE: DNA
<213> ORGANISM: Homo sapiens
<220> FEATURE:
<221> NAME/KEY: Human GPRC6A
<222> LOCATION: (1)..(2781)
<220> FEATURE:
<221> NAME/KEY: Human GPRC6A
<222> LOCATION: (1)..(2781)
<223> OTHER INFORMATION: Human GPRC6A nucleotide sequence

<400> SEQUENCE: 3

```
atggcattct taattatact aattacctgc tttgtgatta ttcttgctac ttcacagcct      60
tgccagaccc ctgatgactt tgtggctgcc acttctccgg acatatcat aattggaggt     120
ttgtttgcta ttcatgaaaa aatgttgtcc tcagaagact ctcccagacg accacaaatc    180
caggagtgtg ttggctttga aatatcagtt tttcttcaaa ctcttgccat gatacacagc    240
attgagatga tcaacaattc aacactctta cctggagtca aactggggta tgaaatctat    300
gacacttgta cagaagtcac agtggcaatg cagccactc tgaggtttct ttctaaattc     360
aactgctcca gagaaactgt ggagtttaag tgtgactatt ccagctacat gccaagagtt    420
aaggctgtca taggttctgg gtactcagaa ataactatgg ctgtctccag gatgttgaat    480
ttacagctca tgccacaggt gggttatgaa tcaactgcag aaatcctgag tgacaaaatt    540
cgctttcctt cattttacg gactgtgccc agtgacttcc atcaaattaa agcaatggct    600
cacctgattc agaaatctgg ttggaactgg attggcatca taaccacaga tgatgactat    660
ggacgattgg ctcttaacac ttttataatt caggctgaag caaataacgt gtgcatagcc    720
ttcaaagagg ttcttccagc cttctcttca gataatacca ttgaagtcag aatcaatcgg    780
acactgaaga aaatcatttt agaagcccag gttaatgtca ttgtggtatt tctgaggcaa    840
ttccatgttt ttgatctctt caataaagcc attgaaatga atataaataa gatgtggatt    900
gctagtgata ttggtcaac tgccaccaag attaccacca ttcctaatgt taaaaagatt     960
ggcaaagttg tagggtttgc ctttagaaga gggaatatat cctctttcca ttcctttctt   1020
caaaatctgc acttgcttcc cagtgacagt cacaaactct acatgaata tgccatgcat    1080
ttatctgcct gcgcatatgt caaggacact gatttgagtc aatgcatatt caatcattct   1140
caaaggactt tggcctacaa ggctaacaag gctatagaaa ggaacttcgt catgagaaat   1200
gacttcctct gggactatgc tgagccagga ctcattcata gtattcagct tgcagtgttt   1260
gcccttggtt atgccattcg ggatctgtgt caagctcgtg actgtcagaa ccccaacgcc   1320
tttcaaccat gggagttact tggtgtgcta aaaaatgtga cattcactga tggatggaat   1380
tcatttcatt ttgatgctca cggggattta aatactggat atgatgttgt gctctggaag   1440
gagatcaatg gacacatgac tgtcactaag atggcagaat atgacctaca gaatgatgtc   1500
ttcatcatcc cagatcagga aacaaaaaat gagttcagga tcttaagca aattcaatct   1560
aaatgctcca aggaatgcag tcctgggcaa atgaagaaaa ctacaagaag tcaacacatc   1620
tgttgctatg aatgtcagaa ctgtcctgaa atcattaca ctaatcagac agatatgcct   1680
cactgccttt tatgcaacaa caaaactcac tgggcccctg ttaggagcac tatgtgcttt   1740
gaaaaggaag tggaatatct caactggaat gactccttgg ccatcctact cctgattctc   1800
tccctactgg gaatcatatt tgttctggtt gttggcataa tatttacaag aaacctgaac   1860
acacctgttg tgaaatcatc cgggggatta agagtctgct atgtgatcct tctctgtcat   1920
ttcctcaatt ttgccagcac gagcttttc attggagaac cacaagactt cacatgtaaa   1980
accaggcaga caatgtttgg agtgagcttt actctttgca tctcctgcat tttgacgaag   2040
tctctgaaaa ttttgctagc cttcagcttt gatcccaaat tacagaaatt tctgaagtgc   2100
ctctatagac cgatccttat tatcttcact tgcacgggca tccaggttgt catttgcaca   2160
ctctggctaa tctttgcagc acctactgta gaggtgaatg tctccttgcc cagagtcatc   2220
atcctggagt gtgaggaggg atccatactt gcatttggca ccatgctggg ctacattgcc   2280
atcctggcct tcatttgctt catatttgct ttcaaaggca aatatgagaa ttacaatgaa   2340
```

-continued

```
gccaaattca ttacatttgg catgctcatt tacttcatag cttggatcac attcatccct    2400
atctatgcta ccacatttgg caaatatgta ccagctgtgg agattattgt catattaata    2460
tctaactatg gaatcctgta ttgcacattc atccccaaat gctatgttat tatttgtaag    2520
caagagatta acacaaagtc tgcctttctc aagatgatct acagttattc ttcccatagt    2580
gtgagcagca ttgccctgag tcctgcttca ctggactcca tgagcggcaa tgtcacaatg    2640
accaatccca gctctagtgg caagtctgca acctggcaga aaagcaaaga tcttcaggca    2700
caagcatttg cacacatatg cagggaaaat gccacaagtg tatctaaaac tttgcctcga    2760
aaaagaatgt caagtatatg a                                              2781
```

<210> SEQ ID NO 4
<211> LENGTH: 928
<212> TYPE: PRT
<213> ORGANISM: Feline calicivirus
<220> FEATURE:
<221> NAME/KEY: Cat GPRC6A
<222> LOCATION: (1)..(928)
<223> OTHER INFORMATION: Cat GPRC6A amino acid sequence

<400> SEQUENCE: 4

```
Met Ala Leu Leu Ile Thr Leu Ile Thr Cys Phe Val Ile Pro Leu Ala
1               5                   10                  15

Thr Ser Gln Thr Cys Gln Thr Pro Asp Asp Phe Val Ala Ala Thr Ser
            20                  25                  30

Pro Gly His Val Ile Ile Gly Gly Leu Phe Ala Ile His Glu Lys Met
        35                  40                  45

Leu Ser Ser Glu Asp Tyr Pro Arg Arg Pro Glu Ile Gln Lys Cys Val
    50                  55                  60

Gly Phe Glu Ile Ser Ile Phe Leu Gln Thr Leu Ala Met Ile His Ser
65                  70                  75                  80

Ile Glu Met Ile Asn Asn Ser Thr Leu Leu Ser Gly Ile Lys Leu Gly
                85                  90                  95

Tyr Glu Ile Tyr Asp Thr Cys Thr Glu Val Thr Val Ala Met Ala Ala
            100                 105                 110

Ala Leu Arg Phe Leu Ser Lys Phe Asn Ser Ser Arg Glu Ile Met Glu
        115                 120                 125

Phe Lys Cys Asp Tyr Ser Ser Tyr Met Pro Arg Val Lys Ala Val Ile
    130                 135                 140

Gly Ala Gly Tyr Ser Glu Ile Thr Met Ala Val Ser Arg Met Leu Asn
145                 150                 155                 160

Leu Gln Leu Met Pro Gln Val Ser Tyr Glu Ser Thr Ala Glu Ile Leu
                165                 170                 175

Ser Asp Lys Ile Arg Phe Pro Ser Phe Leu Arg Thr Val Pro Ser Asp
            180                 185                 190

Phe Tyr Gln Thr Lys Ala Met Ala His Leu Ile Glu Lys Ser Gly Trp
        195                 200                 205

Asn Trp Ile Gly Ile Ile Ala Thr Asp Asp Tyr Gly Arg Met Ala
    210                 215                 220

Leu Asn Thr Phe Ala Val Gln Thr Thr Ala Asn Asn Val Cys Ile Ala
225                 230                 235                 240

Phe Lys Glu Val Leu Pro Ala Phe Leu Ser Asp Asn Thr Ile Glu Val
                245                 250                 255

Arg Ile Asn Glu Thr Leu Glu Lys Ile Ile Ala Glu Ala Gln Val Asn
            260                 265                 270
```

```
Val Ile Val Val Phe Leu Arg Gln Phe His Val Phe Asn Leu Phe Ser
            275                 280                 285

Lys Ala Leu Glu Arg Asn Ile Asn Lys Ile Trp Ile Ala Ser Asp Asn
    290                 295                 300

Trp Ser Thr Ala Thr Lys Ile Thr Thr Ile Pro Asn Val Lys Arg Ile
305                 310                 315                 320

Gly Lys Val Val Gly Phe Thr Phe Arg Arg Gly Asn Met Ser Ser Phe
                325                 330                 335

His Ser Phe Leu Gln Asn Leu His Ile Phe Pro Ser Asp Asn Asn Lys
            340                 345                 350

Val Leu Asn Glu Tyr Ala Thr Leu Leu Ser Ala Cys Ala Tyr Val Lys
        355                 360                 365

Asp Ser Asp Leu Ser Gln Cys Ile Ser Asn His Ser Gln Gly Thr Leu
    370                 375                 380

Ala Tyr Lys Val Asn Lys Asp Ile Glu Arg Asn Phe Ser Leu Arg Asn
385                 390                 395                 400

Asp Phe Leu Trp Asn Tyr Thr Glu Pro Gly Leu Val His Ser Ile Gln
                405                 410                 415

Leu Ala Val Leu Ala Leu Gly Tyr Ala Ile Arg Asp Leu Cys Gln Ala
            420                 425                 430

Arg Asp Cys Gln Asn Pro Asn Ala Phe Gln Pro Trp Glu Leu Leu Asp
        435                 440                 445

Ala Leu Lys Asn Val Thr Phe Thr Asp Glu Gly Asn Ser Phe His Phe
    450                 455                 460

Asp Ala His Gly Asp Met Asn Thr Gly Tyr Asp Val Val Leu Trp Lys
465                 470                 475                 480

Glu Ile Asp Gly His Leu Thr Ile Thr Lys Ile Ala Gln Tyr Asp Leu
                485                 490                 495

Lys Asn Asp Val Phe Val Ile Thr Asp Gln Glu Thr Lys Asn Glu Phe
            500                 505                 510

Arg Asn Leu Lys Gln Ile Gln Ser Lys Cys Ser Lys Glu Cys Ser Pro
        515                 520                 525

Gly Gln Met Lys Lys Thr Thr Arg Ser Gln His Ile Cys Cys Tyr Glu
    530                 535                 540

Cys Val Asn Cys Pro Glu Asn His Tyr Ser Asn Gln Thr Asp Met Asp
545                 550                 555                 560

His Cys Leu Leu Cys Asn Asn Glu Thr Gln Trp Ala Pro Val Lys Ser
                565                 570                 575

Thr Ala Cys Phe Glu Lys Glu Val Glu Tyr Leu Ser Trp Asn Asp Ser
            580                 585                 590

Leu Ala Ile Leu Leu Leu Ala Leu Ser Leu Leu Gly Ile Met Phe Val
        595                 600                 605

Leu Ala Ile Gly Ile Ile Phe Thr Arg Asn Leu Asn Thr Pro Val Val
    610                 615                 620

Lys Ser Ser Gly Gly Leu Leu Val Cys Tyr Val Ile Leu Leu Cys His
625                 630                 635                 640

Phe Leu Asn Phe Ala Ser Thr Gly Phe Phe Ile Gly Glu Pro Gln Asp
                645                 650                 655

Phe Thr Cys Lys Thr Arg Gln Thr Phe Phe Gly Val Ser Phe Thr Leu
            660                 665                 670

Cys Ile Ser Cys Ile Leu Val Lys Ser Leu Lys Ile Leu Leu Ala Phe
        675                 680                 685

Ser Phe Asp Pro Lys Leu Gln Asn Phe Leu Lys Cys Leu Tyr Lys Pro
```

```
                690             695             700
Ile Pro Ile Ile Phe Ile Cys Thr Gly Ile Gln Val Ala Ile Cys Thr
705                     710                 715                 720

Val Trp Leu Ile Phe Ala Ala Pro Ala Val Glu Glu Asn Val Ser Leu
                    725                 730                 735

Pro Arg Val Ile Ile Leu Glu Cys Glu Gly Ser Ile Leu Ala Phe
                740                 745                 750

Gly Ile Met Leu Gly Tyr Ile Ala Ile Leu Ala Phe Ile Cys Phe Ile
                755                 760                 765

Phe Ala Phe Lys Gly Arg Lys Leu Pro Glu Asn Tyr Asn Glu Ala Lys
770                 775                 780

Phe Ile Thr Phe Gly Met Leu Val Tyr Phe Ile Ala Trp Ile Thr Phe
785                 790                 795                 800

Val Pro Val Tyr Ala Thr Thr Phe Gly Lys Tyr Leu Pro Ala Val Glu
                805                 810                 815

Ile Ile Ile Ile Leu Ile Ser Asn Tyr Gly Ile Leu Cys Cys Thr Phe
                820                 825                 830

Phe Pro Lys Cys Tyr Val Ile Leu Tyr Lys Gln Glu Thr Asn Thr Lys
                835                 840                 845

Ser Ala Phe Leu Lys Met Ile Tyr Ser Tyr Ser Ser His Ser Ala Ser
850                 855                 860

Ser Leu Ala Met Ser His Val Ser Leu Asp Ser Ser Ser Ser Asn Ile
865                 870                 875                 880

Thr Ala Thr Asn Pro Ser Ser Gly Gly Arg Pro Ala Ala Trp Gln Glu
                885                 890                 895

Ser Arg Asp Ile Arg Ala Gln Ala Phe Ala His Thr Arg Arg Glu Asn
                900                 905                 910

Ala Ala Ser Met Ser Lys Thr Trp Pro Arg Lys Arg Ile Ser Ser Ile
                915                 920                 925

<210> SEQ ID NO 5
<211> LENGTH: 928
<212> TYPE: PRT
<213> ORGANISM: Canis familiaris
<220> FEATURE:
<221> NAME/KEY: Dog GPRC6A
<222> LOCATION: (1)..(928)
<223> OTHER INFORMATION: Dog GPRC6A amino acid sequence

<400> SEQUENCE: 5

Met Ala Leu Leu Ile Ile Pro Ile Thr Cys Phe Gly Ser Thr Leu Val
1               5                   10                  15

Thr Ser Gln Pro Cys Gln Thr Pro Asp Asp Phe Val Ala Ala Thr Ser
                20                  25                  30

Pro Gly His Ile Met Ile Gly Gly Leu Phe Ala Ile His Glu Lys Met
            35                  40                  45

Leu Pro Ser Glu Asp Tyr Pro Arg Arg Pro Glu Ile Gln Lys Cys Val
        50                  55                  60

Gly Phe Glu Ile Ser Ile Phe Leu Gln Thr Leu Ala Met Ile His Ser
65                  70                  75                  80

Ile Glu Met Ile Asn Asn Ser Thr Leu Leu Ser Gly Val Lys Leu Gly
                85                  90                  95

Tyr Glu Ile Tyr Asp Thr Cys Thr Glu Val Thr Val Ala Met Ala Ala
                100                 105                 110

Thr Leu Arg Phe Leu Ser Lys Arg Asn Cys Ser Arg Glu Ile Val Glu
            115                 120                 125
```

```
Phe Lys Cys Asp Tyr Ser Ser Tyr Met Pro Arg Val Lys Ala Val Ile
    130                 135                 140

Gly Ala Gly Tyr Ser Glu Ile Thr Met Ala Val Ser Arg Met Leu Asn
145                 150                 155                 160

Leu Gln Leu Met Pro Gln Val Ser Tyr Glu Ser Thr Ala Glu Ile Leu
                165                 170                 175

Ser Asp Lys Ile Arg Phe Pro Ser Phe Leu Arg Thr Val Pro Ser Asp
            180                 185                 190

Phe Tyr Gln Thr Lys Ala Met Ala His Leu Ile Gln Lys Ser Gly Trp
        195                 200                 205

Asn Trp Ile Gly Ile Ile Ala Thr Asp Asp Tyr Gly Arg Leu Ala
    210                 215                 220

Leu Asn Thr Phe Ala Val Gln Thr Ala Ala Asn Asn Val Cys Ile Ala
225                 230                 235                 240

Phe Lys Glu Val Leu Pro Ala Phe Leu Ser Asp Asp Thr Ile Glu Ile
                245                 250                 255

Arg Ile Asn Glu Thr Leu Glu Lys Ile Ile Ala Glu Ala Gln Val Asn
            260                 265                 270

Val Ile Val Val Phe Leu Arg Gln Phe His Val Phe Asn Leu Phe Thr
        275                 280                 285

Lys Ala Ile Glu Lys Asn Ile Asn Lys Ile Trp Ile Ala Ser Asp Asn
290                 295                 300

Trp Ser Met Ala Thr Lys Ile Thr Thr Ile Pro Asn Val Lys Arg Ile
305                 310                 315                 320

Gly Lys Val Val Gly Phe Thr Phe Arg Arg Gly Asn Met Ser Ser Phe
                325                 330                 335

His Ser Phe Leu Gln Asn Leu His Met Phe Pro Arg Asp Asn Asn Lys
            340                 345                 350

Pro Leu Asn Glu Tyr Ala Met Leu Leu Ser Ala Cys Ala His Val Lys
        355                 360                 365

Asp Ser Asp Leu Ser Gln Cys Ile Ser Ser Arg Ser Arg Gly Thr Leu
    370                 375                 380

Ala Tyr Thr Ala Asn Lys Asp Ile Glu Arg Asn Phe Ser Leu Arg Asn
385                 390                 395                 400

Asp Phe Leu Trp Asp Tyr Thr Glu Pro Gly Pro Val His Ser Ile Gln
                405                 410                 415

Leu Ala Val Leu Ala Leu Gly Tyr Ala Ile Arg Asp Leu Cys Gln Ala
            420                 425                 430

Arg Asp Cys Gln Asn Pro Asn Ala Phe Gln Pro Trp Glu Leu Leu Asp
        435                 440                 445

Val Leu Lys Asn Val Thr Phe Thr Asp Glu Gly Asn Ser Phe His Phe
    450                 455                 460

Asp Ala His Gly Asp Met Asn Thr Gly Tyr Asp Val Val Leu Trp Lys
465                 470                 475                 480

Glu Ile Gly Gly His Met Thr Ile Thr Lys Met Ala Gln Tyr Asp Leu
                485                 490                 495

Arg Asn Asp Val Phe Ile Ile Thr Asp Gln Glu Thr Lys Asn Glu Phe
            500                 505                 510

Arg Asn Leu Lys Gln Ile Arg Ser Lys Cys Ser Lys Glu Cys Ser Pro
        515                 520                 525

Gly Gln Met Lys Lys Thr Thr Arg Ser Gln His Ile Cys Cys Tyr Glu
    530                 535                 540
```

```
Cys Val Asp Cys Pro Glu Asn His Tyr Ser Asn Gln Thr Asp Met Asp
545                 550                 555                 560

His Cys Leu Leu Cys Asn Asn Glu Thr His Trp Ala Pro Val Arg Ser
                565                 570                 575

Thr Arg Cys Phe Glu Lys Glu Val Glu Tyr Leu Asn Trp Asn Asp Ser
            580                 585                 590

Leu Ala Ile Leu Leu Leu Ala Leu Ser Leu Leu Gly Ile Ile Leu Val
        595                 600                 605

Leu Ala Ile Gly Ile Ile Phe Thr Arg Asn Leu Asn Thr Pro Ile Val
        610                 615                 620

Lys Ser Ser Gly Gly Leu Leu Val Cys Tyr Val Ile Leu Leu Cys His
625                 630                 635                 640

Val Leu Asn Phe Ala Ser Thr Gly Phe Phe Ile Gly Glu Pro Gln Asp
                645                 650                 655

Phe Thr Cys Lys Thr Arg Gln Thr Val Phe Gly Val Ser Phe Thr Leu
            660                 665                 670

Cys Ile Ser Cys Ile Leu Met Lys Ser Leu Lys Ile Leu Leu Ala Phe
        675                 680                 685

Ser Phe Asp Pro Lys Leu Gln Asn Phe Leu Lys Cys Leu Tyr Lys Pro
690                 695                 700

Ile Pro Ile Ile Phe Thr Cys Thr Gly Ile Gln Val Val Ile Cys Thr
705                 710                 715                 720

Ile Trp Leu Ile Phe Ala Ala Pro Ala Val Glu Glu Asn Val Ser Leu
                725                 730                 735

Pro Arg Val Ile Ile Leu Glu Cys Glu Glu Gly Ser Val Leu Ala Phe
            740                 745                 750

Gly Thr Met Leu Gly Tyr Ile Ala Ile Leu Ala Phe Ile Cys Phe Ile
        755                 760                 765

Phe Ala Phe Lys Gly Arg Lys Leu Pro Glu His Tyr Asn Glu Ala Lys
770                 775                 780

Phe Ile Thr Phe Gly Met Leu Ile Tyr Phe Ile Ala Trp Ile Thr Phe
785                 790                 795                 800

Ile Pro Ile Tyr Ala Thr Thr Phe Gly Lys Tyr Leu Pro Ala Val Glu
                805                 810                 815

Ile Ile Val Ile Leu Ile Ser Asn Tyr Gly Ile Leu Cys Cys Thr Phe
            820                 825                 830

Phe Pro Lys Cys Tyr Ile Ile Leu Cys Lys Gln Glu Ala Asn Thr Lys
        835                 840                 845

Ser Ala Phe Leu Lys Met Ile Tyr Ser Tyr Ser Ser His Thr Ala Ser
850                 855                 860

Ser Leu Ala Ile Ser His Val Ser Leu Asp Ser Thr Asn Ser Ser Ile
865                 870                 875                 880

Thr Thr Thr Asn Pro Ser Ser Gly Lys Ser Ala Ala Trp Gln Glu
                885                 890                 895

Ser Lys Asp Leu Gln Ala Gln Ala Phe Ala His Ile Cys Arg Glu Asn
            900                 905                 910

Ala Ile Ser Val Pro Lys Ile Leu Pro Arg Lys Arg Ile Ser Ser Ile
        915                 920                 925
```

<210> SEQ ID NO 6
<211> LENGTH: 926
<212> TYPE: PRT
<213> ORGANISM: Homo sapiens
<220> FEATURE:
<221> NAME/KEY: Human GPRC6A
<222> LOCATION: (1)..(926)
<223> OTHER INFORMATION: Human GPRC6A amino acid seqeunce

<400> SEQUENCE: 6

```
Met Ala Phe Leu Ile Ile Leu Ile Thr Cys Phe Val Ile Ile Leu Ala
1               5                   10                  15

Thr Ser Gln Pro Cys Gln Thr Pro Asp Asp Phe Val Ala Ala Thr Ser
            20                  25                  30

Pro Gly His Ile Ile Ile Gly Gly Leu Phe Ala Ile His Glu Lys Met
        35                  40                  45

Leu Ser Ser Glu Asp Ser Pro Arg Arg Pro Gln Ile Gln Glu Cys Val
50                  55                  60

Gly Phe Glu Ile Ser Val Phe Leu Gln Thr Leu Ala Met Ile His Ser
65                  70                  75                  80

Ile Glu Met Ile Asn Asn Ser Thr Leu Leu Pro Gly Val Lys Leu Gly
                85                  90                  95

Tyr Glu Ile Tyr Asp Thr Cys Thr Glu Val Thr Val Ala Met Ala Ala
            100                 105                 110

Thr Leu Arg Phe Leu Ser Lys Phe Asn Cys Ser Arg Glu Thr Val Glu
        115                 120                 125

Phe Lys Cys Asp Tyr Ser Ser Tyr Met Pro Arg Val Lys Ala Val Ile
130                 135                 140

Gly Ser Gly Tyr Ser Glu Ile Thr Met Ala Val Ser Arg Met Leu Asn
145                 150                 155                 160

Leu Gln Leu Met Pro Gln Val Gly Tyr Glu Ser Thr Ala Glu Ile Leu
                165                 170                 175

Ser Asp Lys Ile Arg Phe Pro Ser Phe Leu Arg Thr Val Pro Ser Asp
            180                 185                 190

Phe His Gln Ile Lys Ala Met Ala His Leu Ile Gln Lys Ser Gly Trp
        195                 200                 205

Asn Trp Ile Gly Ile Ile Thr Thr Asp Asp Tyr Gly Arg Leu Ala
210                 215                 220

Leu Asn Thr Phe Ile Ile Gln Ala Glu Ala Asn Asn Val Cys Ile Ala
225                 230                 235                 240

Phe Lys Glu Val Leu Pro Ala Phe Leu Ser Asp Asn Thr Ile Glu Val
                245                 250                 255

Arg Ile Asn Arg Thr Leu Lys Lys Ile Ile Leu Glu Ala Gln Val Asn
            260                 265                 270

Val Ile Val Val Phe Leu Arg Gln Phe His Val Phe Asp Leu Phe Asn
        275                 280                 285

Lys Ala Ile Glu Met Asn Ile Asn Lys Met Trp Ile Ala Ser Asp Asn
290                 295                 300

Trp Ser Thr Ala Thr Lys Ile Thr Thr Ile Pro Asn Val Lys Lys Ile
305                 310                 315                 320

Gly Lys Val Val Gly Phe Ala Phe Arg Arg Gly Asn Ile Ser Ser Phe
                325                 330                 335

His Ser Phe Leu Gln Asn Leu His Leu Leu Pro Ser Asp Ser His Lys
            340                 345                 350

Leu Leu His Glu Tyr Ala Met His Leu Ser Ala Cys Ala Tyr Val Lys
        355                 360                 365

Asp Thr Asp Leu Ser Gln Cys Ile Phe Asn His Ser Gln Arg Thr Leu
370                 375                 380

Ala Tyr Lys Ala Asn Lys Ala Ile Glu Arg Asn Phe Val Met Arg Asn
385                 390                 395                 400
```

```
Asp Phe Leu Trp Asp Tyr Ala Glu Pro Gly Leu Ile His Ser Ile Gln
                405                 410                 415

Leu Ala Val Phe Ala Leu Gly Tyr Ala Ile Arg Asp Leu Cys Gln Ala
            420                 425                 430

Arg Asp Cys Gln Asn Pro Asn Ala Phe Gln Pro Trp Glu Leu Leu Gly
            435                 440                 445

Val Leu Lys Asn Val Thr Phe Thr Asp Gly Trp Asn Ser Phe His Phe
        450                 455                 460

Asp Ala His Gly Asp Leu Asn Thr Gly Tyr Asp Val Val Leu Trp Lys
465                 470                 475                 480

Glu Ile Asn Gly His Met Thr Val Thr Lys Met Ala Glu Tyr Asp Leu
                485                 490                 495

Gln Asn Asp Val Phe Ile Ile Pro Asp Gln Glu Thr Lys Asn Glu Phe
            500                 505                 510

Arg Asn Leu Lys Gln Ile Gln Ser Lys Cys Ser Lys Glu Cys Ser Pro
        515                 520                 525

Gly Gln Met Lys Lys Thr Thr Arg Ser Gln His Ile Cys Cys Tyr Glu
        530                 535                 540

Cys Gln Asn Cys Pro Glu Asn His Tyr Thr Asn Gln Thr Asp Met Pro
545                 550                 555                 560

His Cys Leu Leu Cys Asn Asn Lys Thr His Trp Ala Pro Val Arg Ser
                565                 570                 575

Thr Met Cys Phe Glu Lys Glu Val Glu Tyr Leu Asn Trp Asn Asp Ser
            580                 585                 590

Leu Ala Ile Leu Leu Leu Ile Leu Ser Leu Leu Gly Ile Ile Phe Val
            595                 600                 605

Leu Val Val Gly Ile Ile Phe Thr Arg Asn Leu Asn Thr Pro Val Val
        610                 615                 620

Lys Ser Ser Gly Gly Leu Arg Val Cys Tyr Val Ile Leu Leu Cys His
625                 630                 635                 640

Phe Leu Asn Phe Ala Ser Thr Ser Phe Phe Ile Gly Glu Pro Gln Asp
                645                 650                 655

Phe Thr Cys Lys Thr Arg Gln Thr Met Phe Gly Val Ser Phe Thr Leu
            660                 665                 670

Cys Ile Ser Cys Ile Leu Thr Lys Ser Leu Lys Ile Leu Leu Ala Phe
        675                 680                 685

Ser Phe Asp Pro Lys Leu Gln Lys Phe Leu Lys Cys Leu Tyr Arg Pro
        690                 695                 700

Ile Leu Ile Ile Phe Thr Cys Thr Gly Ile Gln Val Val Ile Cys Thr
705                 710                 715                 720

Leu Trp Leu Ile Phe Ala Ala Pro Thr Val Glu Val Asn Val Ser Leu
                725                 730                 735

Pro Arg Val Ile Ile Leu Glu Cys Glu Glu Gly Ser Ile Leu Ala Phe
            740                 745                 750

Gly Thr Met Leu Gly Tyr Ile Ala Ile Leu Ala Phe Ile Cys Phe Ile
        755                 760                 765

Phe Ala Phe Lys Gly Lys Tyr Glu Asn Tyr Asn Glu Ala Lys Phe Ile
        770                 775                 780

Thr Phe Gly Met Leu Ile Tyr Phe Ile Ala Trp Ile Thr Phe Ile Pro
785                 790                 795                 800

Ile Tyr Ala Thr Thr Phe Gly Lys Tyr Val Pro Ala Val Glu Ile Ile
                805                 810                 815
```

-continued

```
Val Ile Leu Ile Ser Asn Tyr Gly Ile Leu Tyr Cys Thr Phe Ile Pro
            820             825                 830

Lys Cys Tyr Val Ile Ile Cys Lys Gln Glu Ile Asn Thr Lys Ser Ala
        835             840                 845

Phe Leu Lys Met Ile Tyr Ser Tyr Ser Ser His Ser Val Ser Ser Ile
    850             855             860

Ala Leu Ser Pro Ala Ser Leu Asp Ser Met Ser Gly Asn Val Thr Met
865             870             875                         880

Thr Asn Pro Ser Ser Ser Gly Lys Ser Ala Thr Trp Gln Lys Ser Lys
            885             890                     895

Asp Leu Gln Ala Gln Ala Phe Ala His Ile Cys Arg Glu Asn Ala Thr
            900             905                 910

Ser Val Ser Lys Thr Leu Pro Arg Lys Arg Met Ser Ser Ile
        915             920             925
```